United States Patent [19]

Kusanagi et al.

[11] Patent Number: 5,215,643
[45] Date of Patent: Jun. 1, 1993

[54] ELECTROCHEMICAL GAS SENSOR

[75] Inventors: Shigekazu Kusanagi; Toru Fujioka; Ayumu Yasuda; Noriyuki Yamaga; Yoshifumi Watabe; Kenji Doi; Keiji Kakite; Koichi Aizawa; Hitoshi Kanagawa, all of Kadoma, Japan

[73] Assignee: Matsushita Electric Works, Ltd., Osaka, Japan

[21] Appl. No.: 364,437

[22] PCT Filed: Feb. 23, 1989

[86] PCT No.: PCT/JP89/00182

§ 371 Date: Apr. 28, 1989

§ 102(e) Date: Apr. 28, 1989

[87] PCT Pub. No.: WO89/08249

PCT Pub. Date: Sep. 8, 1989

[30] Foreign Application Priority Data

| Feb. 24, 1988 | [JP] | Japan | 63-42843 |
| Feb. 24, 1988 | [JP] | Japan | 63-42847 |
| Feb. 24, 1988 | [JP] | Japan | 63-42848 |
| May 13, 1988 | [JP] | Japan | 63-117839 |
| Jul. 26, 1988 | [JP] | Japan | 63-187505 |

[51] Int. Cl.⁵ .................................... G01N 27/407
[52] U.S. Cl. ................................... 204/412; 204/415; 204/424; 204/426; 204/431
[58] Field of Search ............... 204/412, 400, 421, 424, 204/431, 432, 415, 426

[56] References Cited

U.S. PATENT DOCUMENTS

| 4,020,830 | 5/1977 | Johnson et al. | 128/2 E |
| 4,171,253 | 10/1979 | Nolan et al. | 204/411 |
| 4,521,290 | 6/1985 | Venkatasetty | 204/412 |
| 4,795,543 | 1/1989 | Setter et al. | 204/412 |
| 4,812,221 | 3/1989 | Madou et al. | 204/412 |
| 4,865,717 | 9/1989 | Setter et al. | 204/412 |
| 4,900,405 | 2/1990 | Otagawa et al. | 204/412 |
| 4,913,792 | 4/1990 | Nagata et al. | 204/412 |

FOREIGN PATENT DOCUMENTS

89/01148 2/1989 PCT Int'l Appl. .

OTHER PUBLICATIONS

Translation of JP Utility Model Laid Open 55-64760 (May 1980).

Primary Examiner—T. Tung

[57] ABSTRACT

An electrochemical gas sensor comprises an insulating substrate, active and counter electrodes disposed on a surface of the insulating substrate mutually spaced to have respectively reactive portions, a reference electrode spaced from the active and counter electrodes and having a reactive portion, and a solid electrolyte layer formed to cover the reactive portions of the active, counter and reference electrodes, whereby the sensitivity to gases of the active electrode is improved and stabilized.

16 Claims, 20 Drawing Sheets

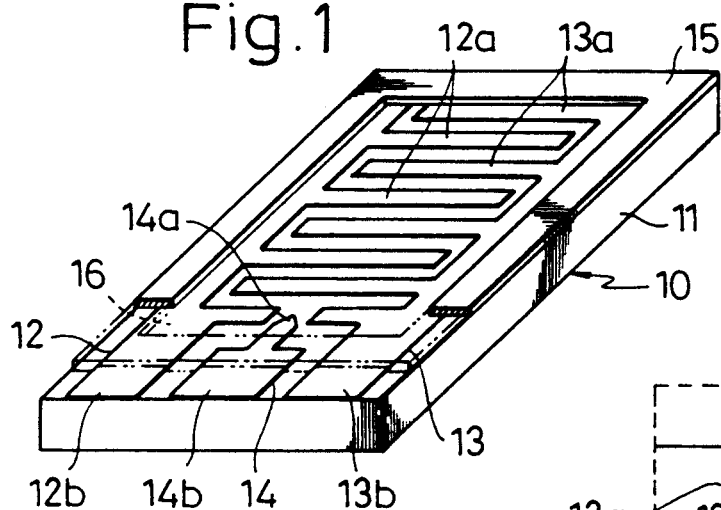
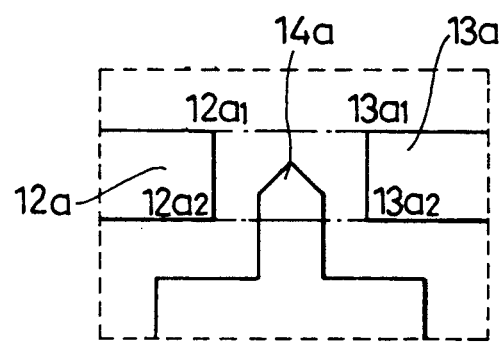
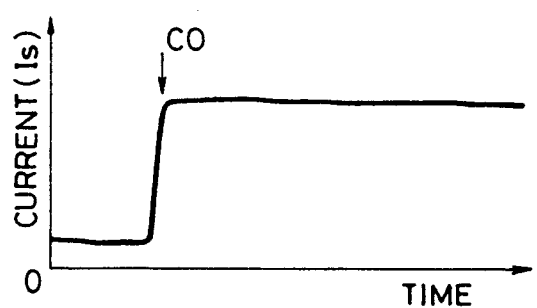
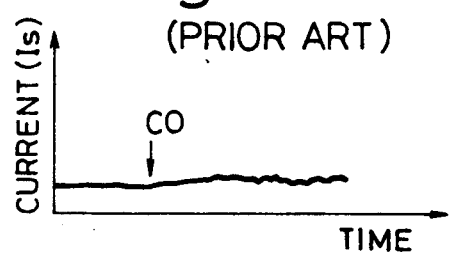
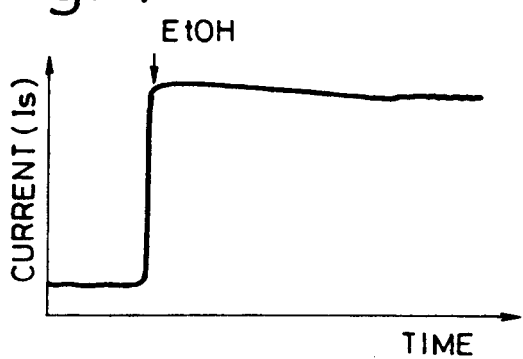
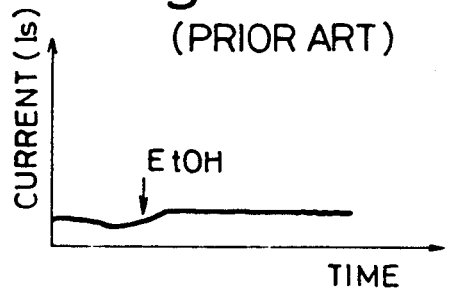

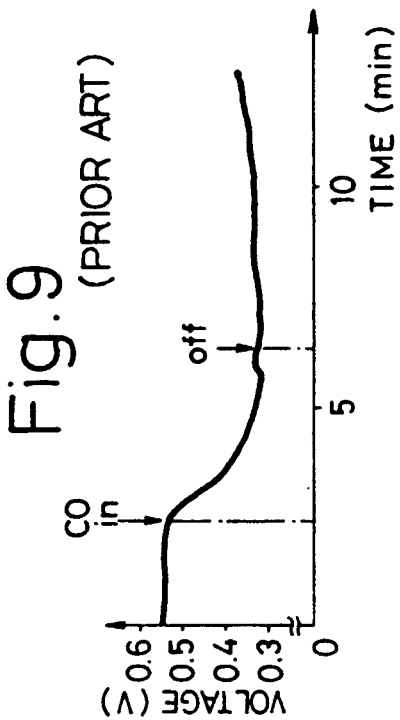
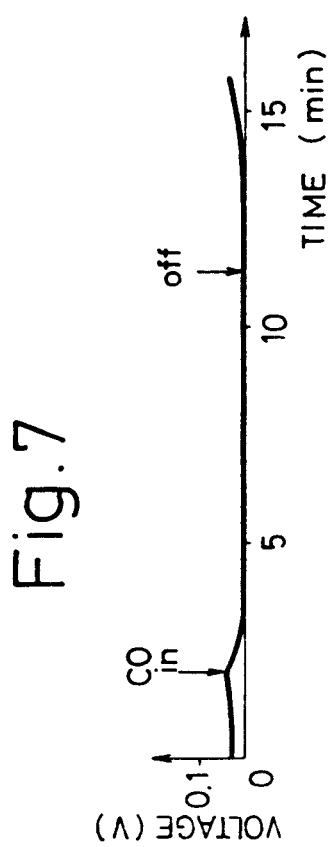
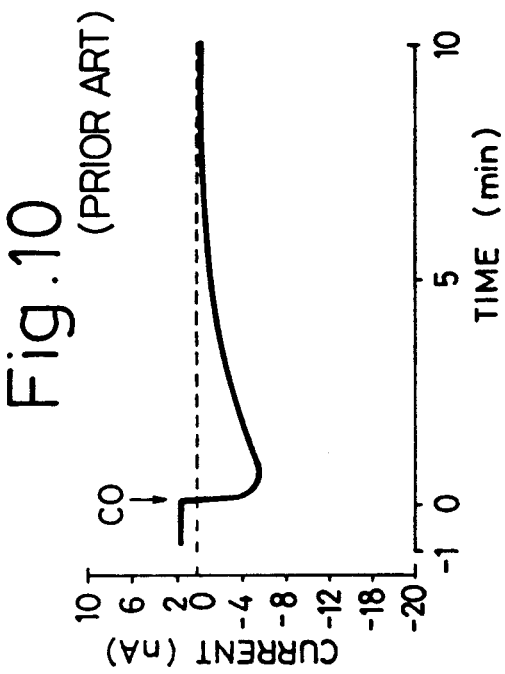
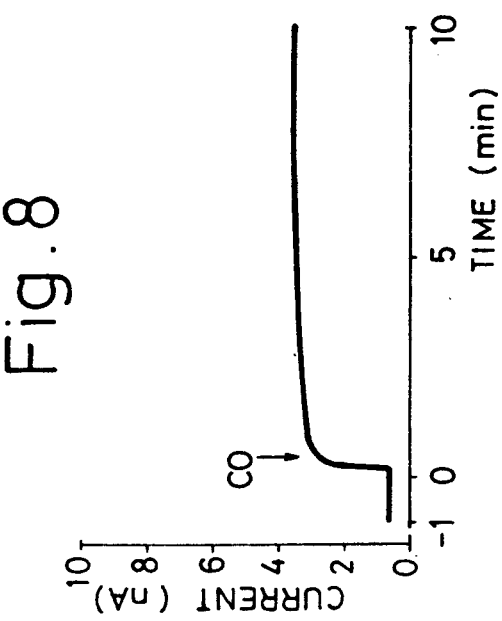

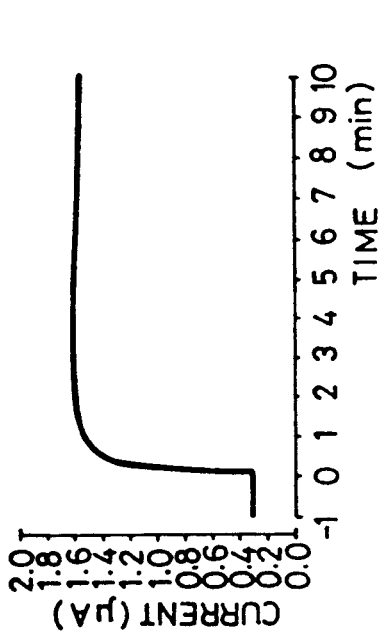
Fig.15
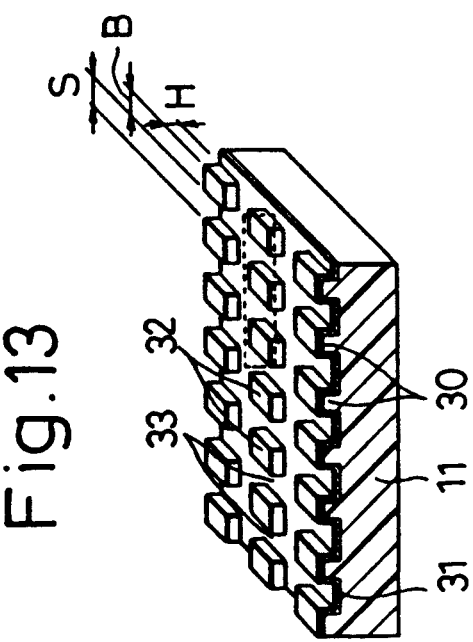
Fig.13
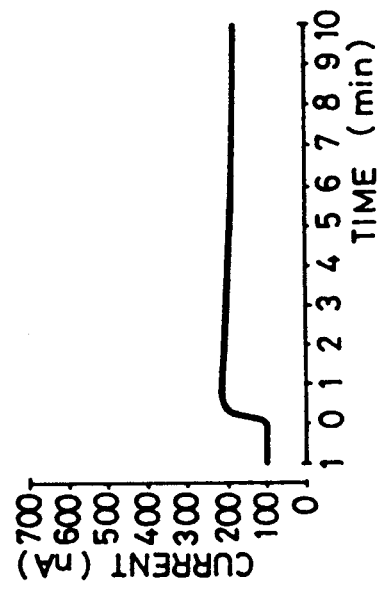
Fig.16
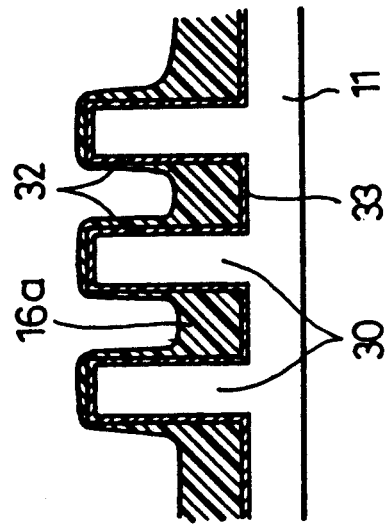
Fig.17
Fig.14

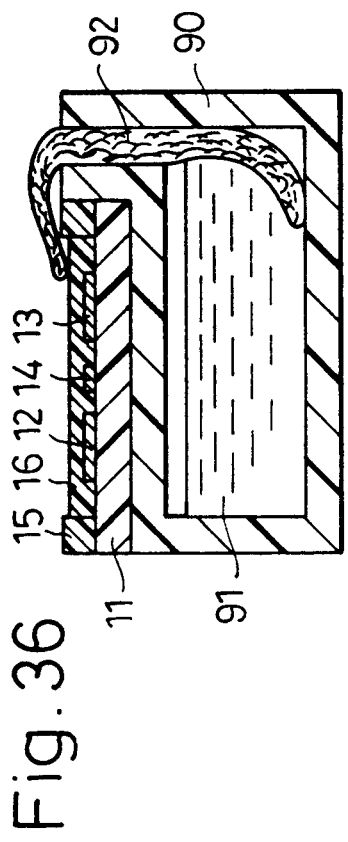
Fig. 32
Fig. 33
Fig. 34
Fig. 35
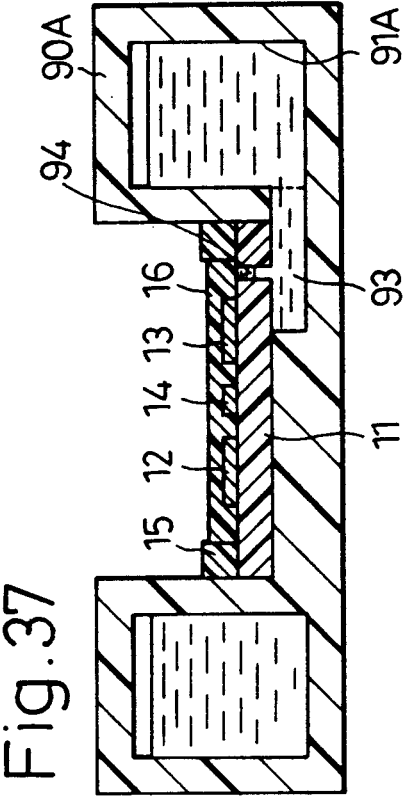
Fig. 36
Fig. 37
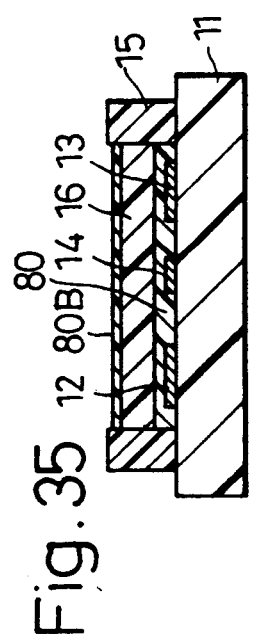
Fig. 38

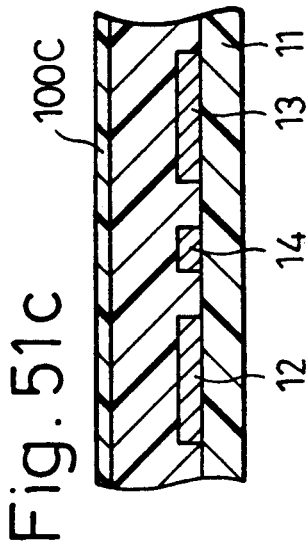
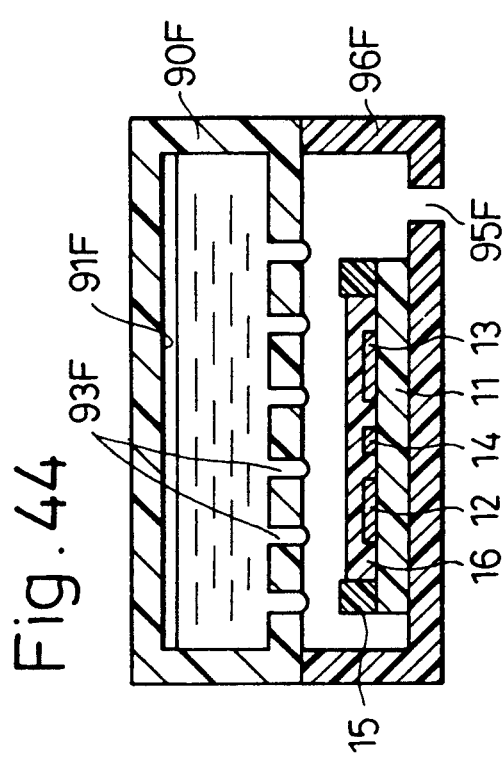
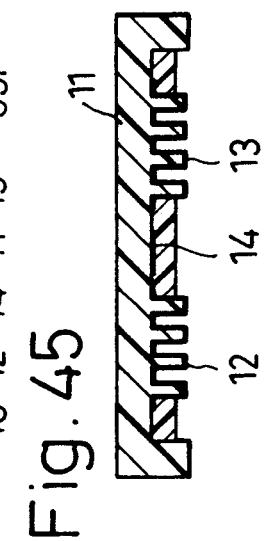

Fig. 54
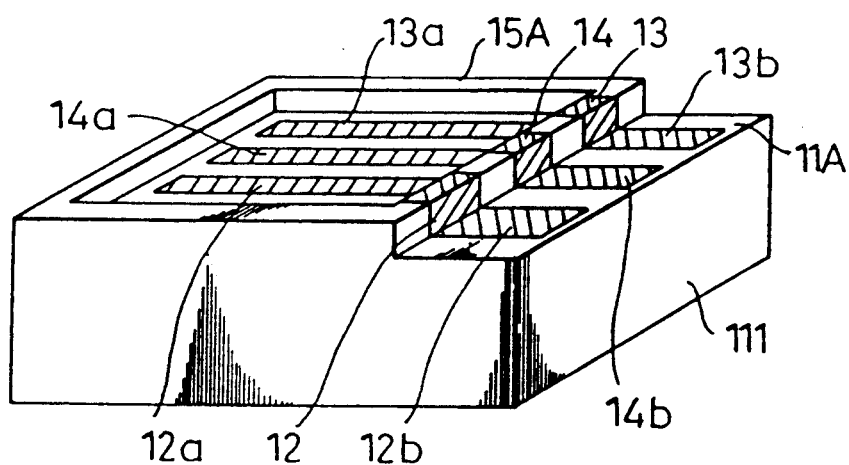
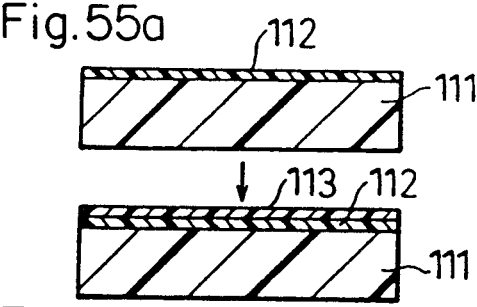
Fig. 55a
Fig. 55b
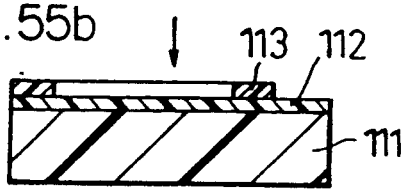
Fig. 55c
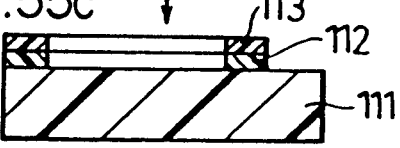
Fig. 55d
Fig. 55e
Fig. 55f
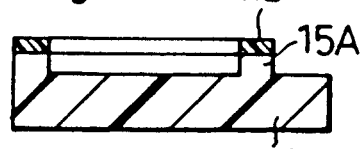
Fig. 55g
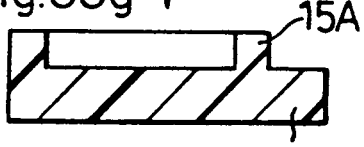
Fig. 55h
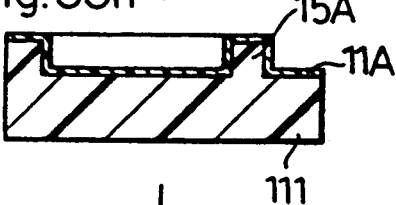
Fig. 55i
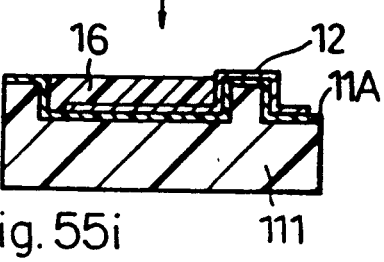

Fig. 56
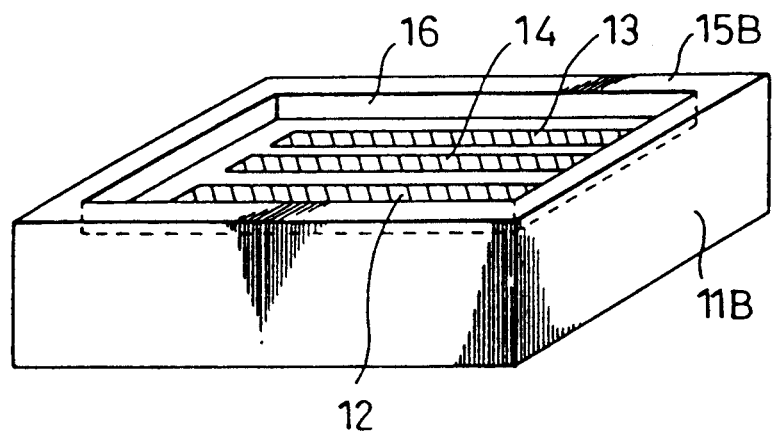
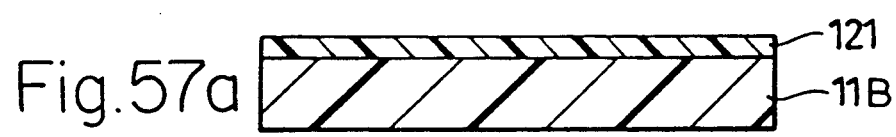
Fig.57a
Fig.57b
Fig.57c
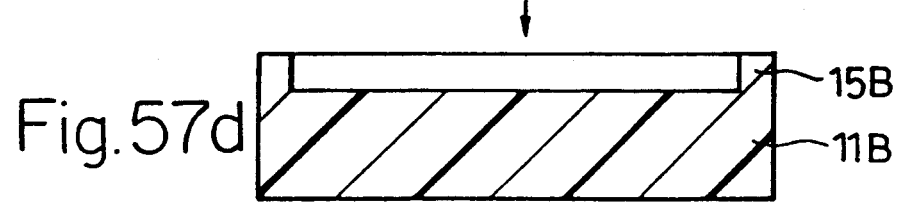
Fig.57d

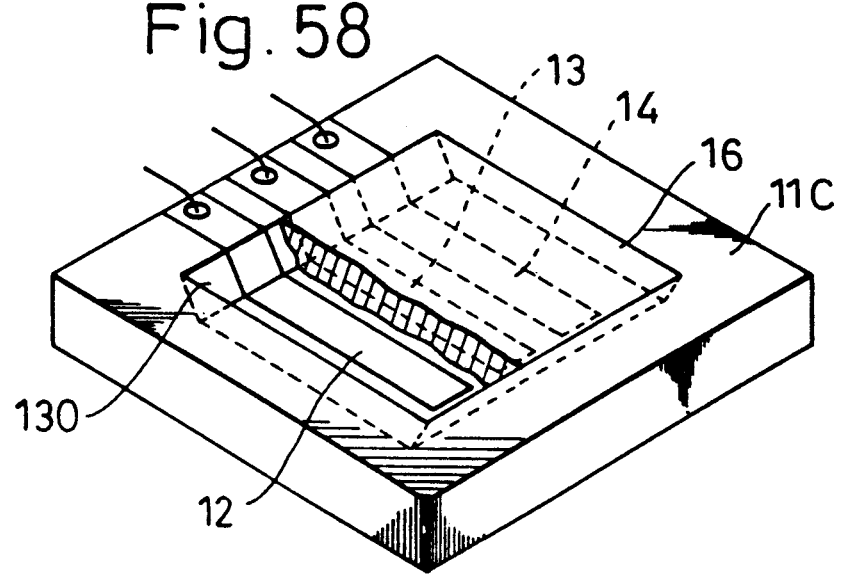
Fig. 58
Fig. 59a
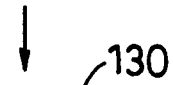
Fig. 59b
Fig. 59c
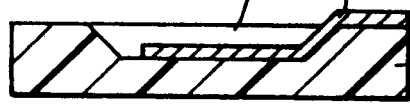
Fig. 59d

Fig. 60
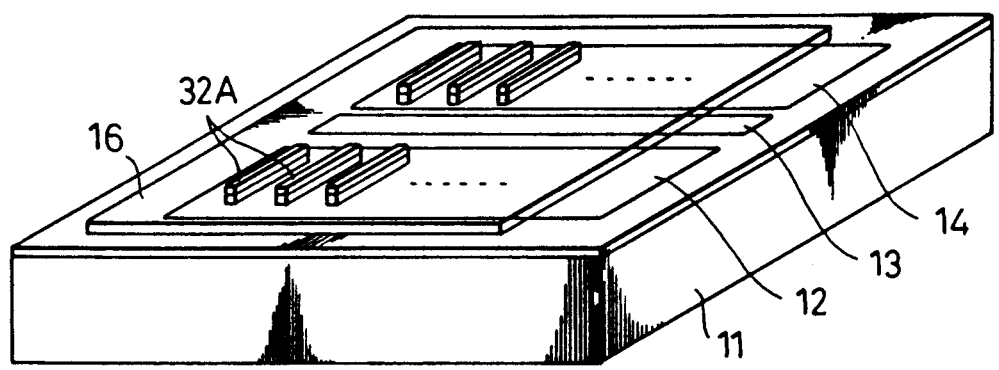
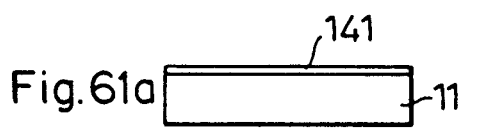
Fig.61a
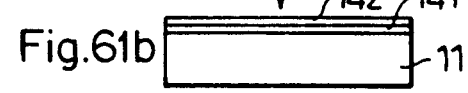
Fig.61b
Fig.61c
Fig.61d
Fig.61e
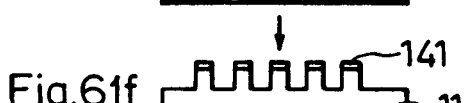
Fig.61f
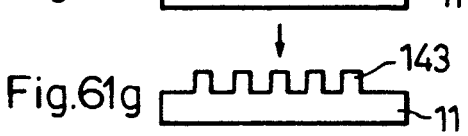
Fig.61g
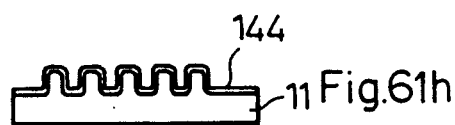
Fig.61h
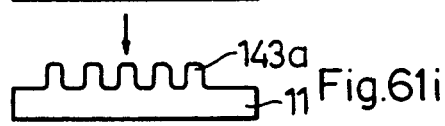
Fig.61i
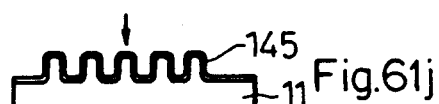
Fig.61j
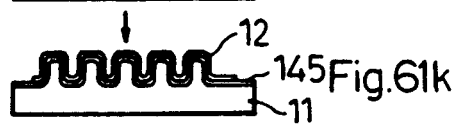
Fig.61k

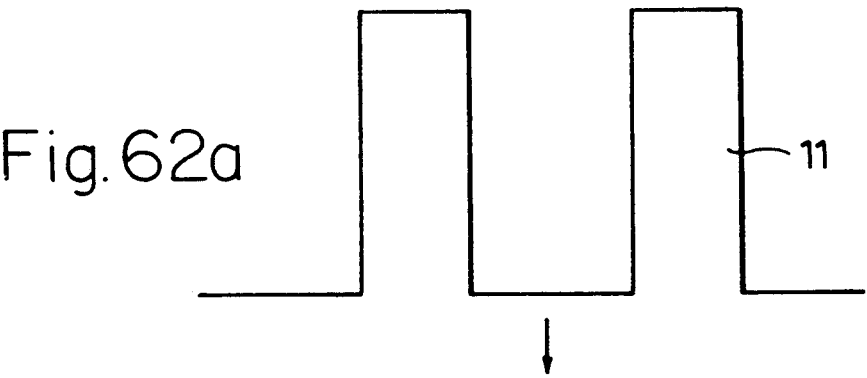
Fig. 62a
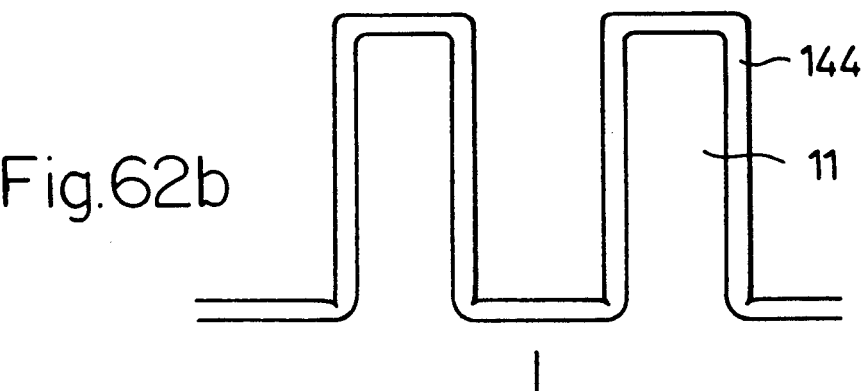
Fig. 62b
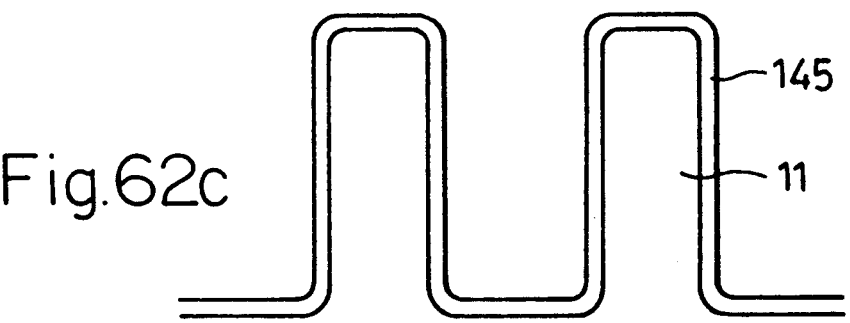
Fig. 62c
Fig. 63
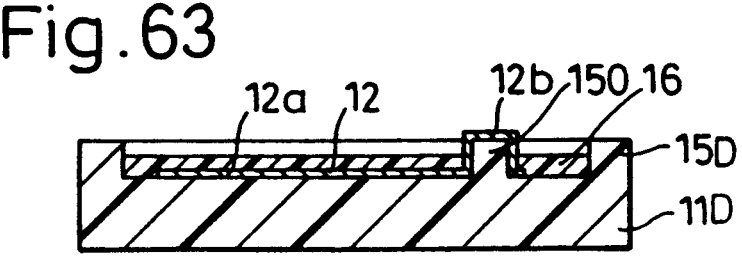

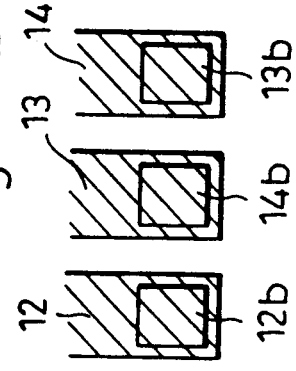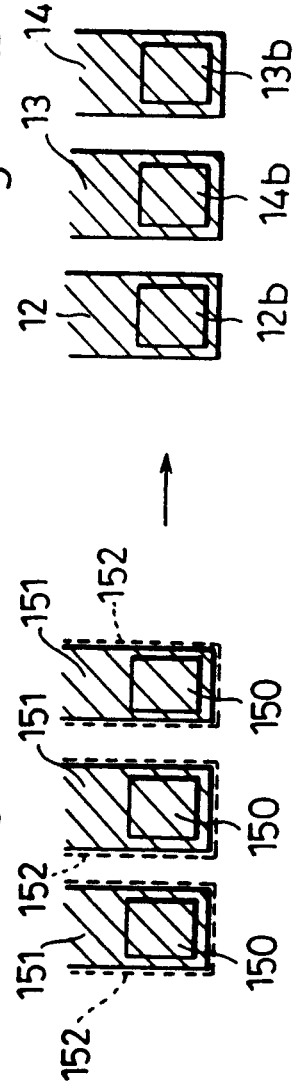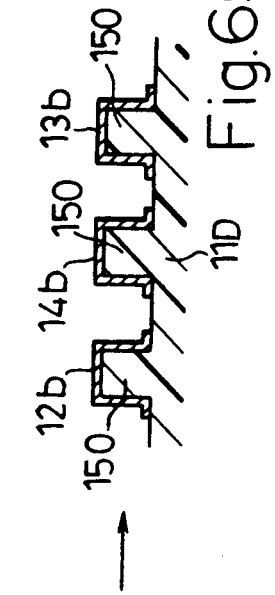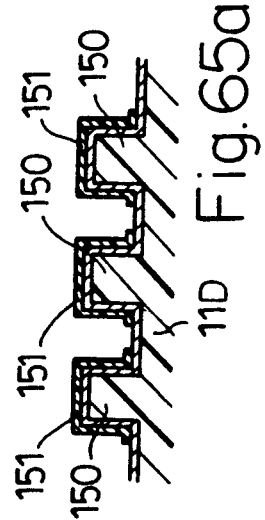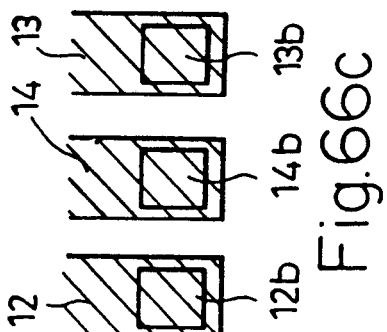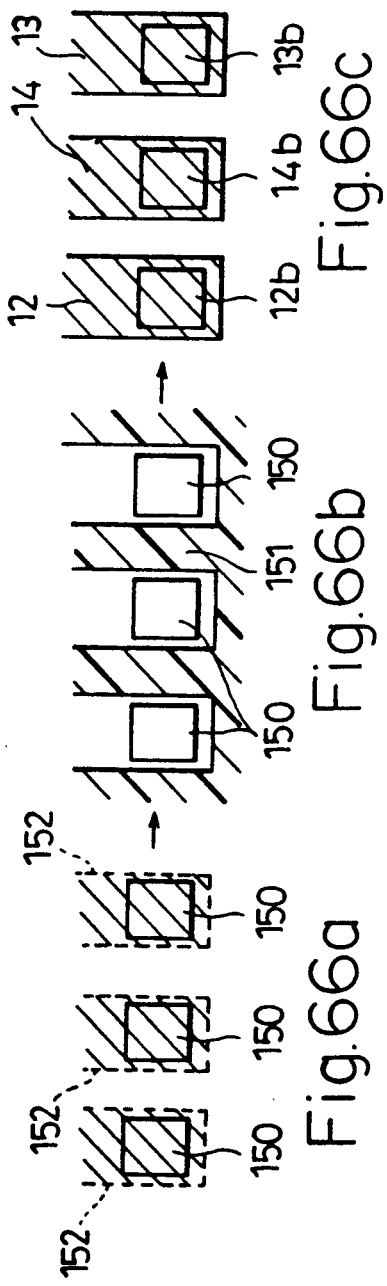

ELECTROCHEMICAL GAS SENSOR

TECHNICAL BACKGROUND OF THE INVENTION

This invention relates to electrochemical gas sensors and, more particularly, to devices electrochemically sensing gases of electrolytic type detecting and determining the quantities of predetermined gas components with an electrolytic reaction utilized.

The electrochemical gas sensors of the kind referred to are high in the sensitivity so that they may be effectively utilized in detecting, for example, industrial use gas concentration, an excessive indoor presence over a predetermined level of such a predetermined gas as CO gas and the like, and so on.

DISCLOSURE OF PRIOR ART

For the electrochemical gas sensors of the kind referred to with the electrolytic reaction utilized, various ones employing an electrochemical element have been suggested in, for example, U.S. Pat. No. 4,227,984 to Russell M. Dempsey et al which showing to employ such polymeric solid electrolyte as sulfonated perfluorocarbon, and U.S. Pat. No. 4,265,714 to Mary E. Nolan et al. In the known electrochemical element, there are provided on one surface of a membrane formed by a solid electrolyte with active and reference electrodes, and on the other surface with an active electrode.

There have arisen various problems, on the other hand, in the foregoing sensors. In particular, for the sensors suggested by Dempsey et al and Nolan et al, they have been defective in that they are difficult to be made compact, thin and minimized in size, the structure of providing the electrodes on both sides of the membrane renders their manufacturing complicated, improper to be mass-produced and to be of high cost, while involving also a problem in respect of characteristic stabilization.

DISCLOSURE OF THE INVENTION

A primary object of the present invention is, therefore, to provide an electrochemical gas sensor which assures a compact arrangement to render the sensor to be thin and small, increases the sensitivity with the ionic conduction remarkably improved, and also increases the durability to a large extent.

According to the present invention, the above object can be attained by providing an electrochemical gas sensor comprising an insulating substrate, active and counter electrodes disposed on one and the same surface of the insulating substrate as mutually spaced and to have respectively reactive portions, a reference electrode provided as spaced from the active and counter electrodes and having a reactive portion, a solid electrolyte layer formed to cover and across at least the reactive portions of the active, counter and reference electrodes, and means giving at least to said active electrode an influence for improving and stabilizing the sensitivity to gases.

Other objects and advantages of the present invention should be made clear in the following description of the invention detailed with reference to preferred embodiments shown in accompanying drawings.

BRIEF EXPLANATION OF THE DRAWINGS

FIG. 1 is a perspective view of the electrochemical gas sensor in an embodiment according to the present invention;

FIG. 2 is a fragmentary plan view as magnified of the sensor shown in FIG. 1;

FIG. 3 is a graph showing a detection current responsive to inflow time of CO gas into the sensor of FIG. 1;

FIG. 4 is a graph showing a detection current responsive to inflow time of ethanol (EtOH) gas into the sensor of FIG. 1;

FIG. 5 is a graph showing a detection current responsive to the CO gas inflow time into a known sensor in which no reference electrode is disposed between the active and counter electrodes;

FIG. 6 is a graph showing a detection current responsive to the EtOH gas inflow time into the same sensor as in FIG. 5;

FIG. 7 is a graph showing a potential of the reference electrode of Au responsive to the CO gas inflow time into the sensor of FIG. 1;

FIG. 8 is a graph showing a detection current responsive to the CO gas inflow time into the sensor having the reference electrode of Au in FIG. 1;

FIG. 9 is a graph showing a potential of the reference electrode of Pt in a known sensor responsive to the CO gas inflow time;

FIG. 10 is a graph showing a detection current responsive to the CO gas inflow time into the known sensor having the reference electrode of Pt;

FIG. 13 is a fragmentary perspective view of another embodiment of the present invention;

FIG. 14 is a fragmentary sectioned view of the sensor of FIG. 13;

FIG. 15 is a graph showing the detection current responsive to the CO gas inflow time into the sensor of FIG. 13;

FIG. 16 is a fragmentary sectioned view of a comparative example of a known sensor;

FIG. 17 is a graph showing a detection current responsive to the CO gas inflow time into the known sensor of FIG. 16;

FIGS. 32 through 37 are sectional views of further embodiments of the present invention;

FIG. 38 shows in a fragmentary sectioned view a still further embodiment of the present invention;

FIGS. 39 through 44 show in sectional views further embodiments of the present invention;

FIG. 45 is a fragmentary sectioned view of still another embodiment of the present invention;

FIGS. 46 through 50 show in sectioned views still further embodiments of the present invention;

FIGS. 51a through 51c are fragmentary sectioned views of the sensor shown in FIG. 50;

FIG. 54 shows in a perspective view still another embodiment of the present invention;

FIGS. 55a through 55i show in sectional views sequential manufacturing steps of the sensor of FIG. 54;

FIG. 56 shows in a perspective view another embodiment of the present invention;

FIGS. 57a through 57d show in sectional views sequential manufacturing steps of the sensor of FIG. 56;

FIG. 58 shows in a perspective view another embodiment of the present invention;

FIGS. 59a through 59d are sectional views showing manufacturing steps of the sensor of FIG. 58;

FIG. 60 shows in a perspective view another embodiment of the present invention;

FIGS. 61a through 61k are sectional views showing manufacturing steps of the sensor of FIG. 60;

FIGS. 62a through 62c are explanatory views for the manufacturing of the sensor of FIG. 60;

FIG. 63 is a sectional view showing still another embodiment of the present invention;

FIGS. 64a and 64b and FIGS. 65a and 65b show in sectioned views respectively manufacturing steps of the sensor shown in FIG. 63; and FIGS. 66a through 66c show also in sectioned views manufacturing steps of the sensor shown in FIG. 63.

Figure 11:
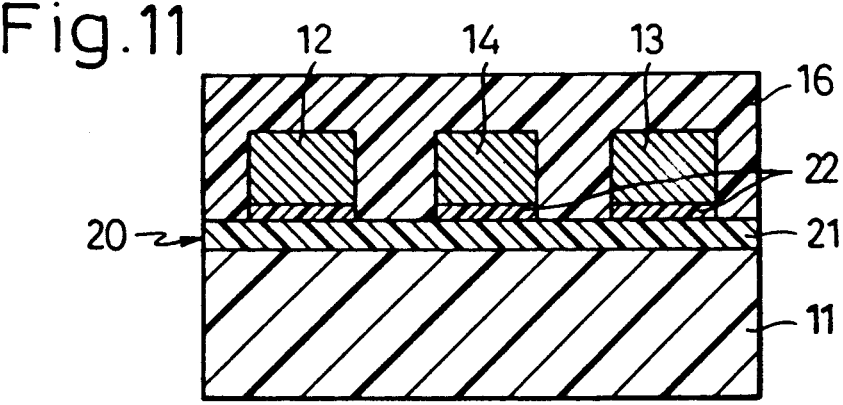
FIG. 11 is a sectional view of another embodiment of the sensor according to the present invention.

While the present invention shall now be explained in detail with reference to the respective embodiments shown in the drawings, it should be appreciated that the intention is not to limit the invention only to these embodiments shown but rather to include all modifications, alterations and equivalent arrangements possible within the scope of the appended claims.

Best Mode for Working the Invention

Referring here to FIGS. 1 and 2, an electrochemical gas sensor 10 according to the present invention comprises a substrate 11 formed by an insulating material and having on one surface a sensing electrode, that is, an active electrode 12, a reverse electrode, that is, counter electrode 13 substantially in parallel to the active electrode 12, and a reference electrode 14 disposed between the active and counter electrodes 12 and 13. The insulating substrate 11 comprises, for example, an alumina ceramics or the like, the active and counter electrodes 12 and 13 are made, for example, by Pt which the reference electrode 14 is made, for example, by Au, and these electrodes may be formed on the insulating substrate 11 by means of such ordinary electrode forming process as sputtering, vacuum deposition or the like process. The active, counter and reference electrodes 12, 13 and 14 respectively include reactive portions 12a, 13a and 14a which participate in an electrochemical action, as well as terminal portions 12b, 13b and 14b for lead-wire connection of the electrodes to an external circuit.

In the present instance, the reactive portions 12a and 13a of the active and counter electrodes 12 and 13 extend from mutually parallel body portions of the electrodes to be comb-teeth shaped and to alternately interdigitate each other while mutually spaced more than 1 μm and, preferably, in a range of about 10 μm to 3 mm. The reactive portion 14a of the reference electrode 14 extends so as to terminate within the opposing space between the reactive portions 12a and 13a, the space being defined by imaginary lines connecting between opposing tip end corners 12a1 and 13a1 as well as 12a2 and 13a2, as shown in FIG. 2.

On the insulating substrate 11, a rectangular frame 15 made of such insulating material as an organic polymer or the like is secured so as to enclose therein the reactive portions 12a and 13a, disposing the terminal portions 12b-14b of the respective electrodes 12-14 outside the frame 15, and a solid electrolyte layer 16 is formed inside the frame 15 so as to cover the respective reactive portions 12a-14a of the electrodes 12-14. For this solid electrolyte layer 16, such high polymer material as perfluorosulfonate polymer (by a U.S. firm DU PONT, Trademark NAFION) or the like, while any other one of such various solid electrolytes as polystyrene sulfonate, polyethylene sulfonate, polyvinyl sulfonate, zirconium phosphate, antimonic acid and the like. In providing the solid electrolyte layer 16, a solution of, for example, perfluorosulfonate polymer in ethanol is applied inside the frame 15 by means of solution cast process and dried.

When the space between the respective reactive portions 12a and 13a of the active and counter electrodes 12 and 13 is too large, it causes IR drop to be increased between the both reactive portions 12a and 13a so that the potential of the reactive portions 12a of the active electrode 12 will vary from a predetermined potential to lower the electrochemical reaction and any sufficient detection current cannot be obtained any more. When, on the other hand, the thickness of the solid electrolyte layer 16 is larger, the ionic conduction inside the electrolyte layer 16 becomes more excellent so as to cause the IR drop between the both reactive portions 12a and 13a of the both active and counter electrodes 12 and 13 to be smaller, whereas it becomes difficult that any detection component passes through the solid electrolyte layer 16 to reach the reactive portions 12a and 13a and it becomes desirable to render the thickness normally to be less than 10 μm.

In the electrochemical gas sensor of the foregoing arrangement, a potentiostat, for example, is connected to the sensor and a fixed voltage of 0.1 V-0.6 V, for example, 0.4 V is applied across the active electrode 12 and the reference electrode 14. When CO gas is present in this state within a detection space for the sensor, the CO gas passes through the solid electrolyte layer 16 of the polymer material to reach the active electrode 12, and a reaction takes place in a following formula (1):

$$CO + H_2O \rightarrow CO_2 \uparrow + 2H^+ + 2e^- \quad (1)$$

At the counter electrode 13, on the other hand, there takes place a reaction of following formula (2):

$$O_2 + 4H^+ + 4e^- \rightarrow 2H_2O \quad (2)$$

Thus produced $H^+$ in the formula (1) flows as a carrier through the solid electrolyte layer 16, so that an electric current output responsive to the concentration of CO is obtained, and the concentration of the CO gas can be detected. In this event, it should be appreciated that the reference electrode 14 is contributive to the potential setting with respect to the active electrode 12. Optimumly, the reactive portion 14a of the reference electrode 14 is disposed between base parts of the reactive portions 12a and 13a of the active and counter electrodes 12, 13, in order to maintain the potential of the reactive portion 12a of the active electrode 12 to be constant to have the socalled potentiostat function achieved. The detection current has been measured by supplying CO gas to the electrochemical gas sensor 10 of the foregoing arrangement of the respective electrodes, and such result as shown in FIG. 3 has been obtained, and the similar measurement with EtOH gas supplied has shown such result as shown in FIG. 4. As will be clear when the results of FIGS. 3 and 4 are compared with test results as in FIG. 5 for a sensor in which the reactive portion of the reference electrode is not disposed between the base parts of the reactive portions of the active and counter electrodes and the CO gas is fed thereto and with similar test results with EtOH gas supplied, the sensor 10 according to the present invention allows a large detection current obtained, and an extremely high sensitivity and reliability can be attained.

It is considered possible, on the other hand, that the active electrode 12 cannot be sufficiently maintained at the constant voltage when the reference electrode 14 is made of Pt, due to that the CO gas which has passed through the solid electrolyte layer 16 and reached the active electrode 12 is also made to reach the reference electrode 14 to cause the electrochemical reaction taken place also at the reference electrode 14. Accordingly, the reference electrode 14 is formed by Au which is low in the gas adsorption, and the electrochemical reaction no more takes place at least on the reference electrode 14. Accordingly, even if the reference electrode 14 is provided concurrently with the active electrode 12, the electrochemical reaction still takes place at the active electrode 12 while no remarkable electrochemical reaction takes place at the reference electrode 14 disposed closer to the active electrode 12, and the active electrode 12 can be effectively maintained at a constant voltage.

Reactivity tests with respect to the CO gas in respect of the foregoing reference electrode 14 of Au have proved that, as shown in FIG. 7, the potential of the reference electrode 14 varies only in a range from 0.04 V/SCE to 0.00 V/SCE even in the presence of CO. Accordingly, as will be clear from a comparison with FIG. 9 showing results of similar tests carried out with respect to a reference electrode made of Pt in which the potential is unstable as varying between 0.55 V/SCE and 0.32 V/SCE, the Au-made reference electrode 14 can be provided with a high stability. In carrying out the respective reactivity tests, an ordinary electrochemical measuring process has been employed, and potential variation of the respective electrodes with respect to SCE (saturated calomel electrode) upon feeding of the CO gas was measured by means of a potentiometer or the like and recorded in a recorder. In this measurement, an aqueous solution of $H_2SO_4$ was employed as the electrolyte of test bath, and SCE and the test bath were made to communicate with each other through KCl salt bridge. As the CO gas, a gas containing 20% CO in the air was led into the test bath. While in the above only the detection of CO gas has been referred to as an example, the same results should be attained also for $H_2$, NO, $NO_2$ and the like gases.

Further, measurements of the detection current responsive to the CO gas quantitatively supplied to the electrochemical gas sensor 10 employing the reference electrode 14 made of Au have been shown to be substantially constant as shown in FIG. 8 and, as will be clear when same is compared with FIG. 10 showing results of similar measurements with respect to an electrochemical sensor employing a Pt-made reference electrode, the former sensor has shown that an accurate detection current can be obtained without showing any abnormal sensitivity, and the gas sensor 10 can be improved in the reliability.

In the foregoing electrochemical gas sensor 10 as has been described, further, the active electrode 12, counter electrode 13 and reference electrode 14 are all disposed on one and the same surface of the insulating substrate 11, it should be appreciated that the formation of these electrodes as well as the solid electrolyte layer 16 can be attained at an extremely high efficiency with such microsize working technology as planar technique and so on employed, so that the sensor can be made thin and minimized in size while attaining highly efficient performance.

According to another feature of the present invention, there can be taken a measure for increasing the bonding ability between the insulating substrate 11 and the electrode made of Pt or Au which show inherently insufficient bonding performance. Referring in detail to this feature by references to FIG. 11, there is formed an intermediate bonding layer 21 showing excellent bonding ability to the substrate 11 and a relatively high resistance value between the insulating substrate 11 and the acting, counter and reference electrodes 12, 13 and 14. Further, it is assumed that a metallic compound layer 22 of a metal material consisting of respective materials forming the respective electrodes and the intermediate bonding layer 21 is further formed between boundary surfaces of the respective electrodes and the intermediate bonding layer 21. With these arrangements, a rigid bonding can be attained between the insulating substrate 11 and intermediate bonding layer 21, between the intermediate bonding layer 21 and the respective electrodes 12-14 or metallic compound layer 22, and between the metallic compound layer 22 and each of the electrodes 12-14, and eventually the insulating substrate 11 and respective electrodes 12-14 can be rigidly integrated. In this case, the intermediate bonding layer 21 is of a high resistance so as not to allow any electric current to flow therethrough to eliminate the so-called battery effect, so that any material of the layer 21 can be prevented from being dissolved into the solid electrolyte layer 16 and any risk of its peeling off from the substrate 11 can be restrained.

Figure 12A:
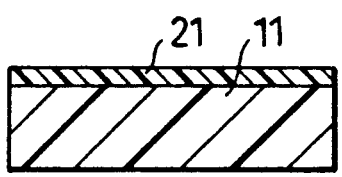
FIGS. 12a through 12f are diagrams showing in sectional views sequential manufacturing steps of the sensor of FIG. 11.

Referring to manufacturing steps of the electrochemical gas sensor 20 of FIG. 11, the high resistance intermediate bonding layer 21 consisting of a polycrystalline silicon is first formed on the insulating substrate heated to be preferably about 300° C. as shown in FIG. 12a, by means of a high frequency sputtering process to be about 500 Å thick. This intermediate bonding layer 21 of polycrystalline silicon is made to have a specific resistance of about $10^9$ to $10^{10}$ $\Omega$.cm. Next, on the intermediate bonding layer 21 and over the entire surface thereof, an electrode layer 23 of Pt is formed by means also of the high frequency sputtering process to be about 5000 Å thick, as in FIG. 12b. Upon the formation of the Pt-made electrode layer 23 by the high frequency sputtering process on the intermediate bonding layer 21 of the polycrystalline silicon, it is considered that there arises a low temperature solid phase reaction between Pt and the polycrystalline silicon due to silicon surface heating by means of high energy particles and so on during the sputtering process, whereby a metallic compound layer 22 of Pt and the silicon is formed at the boundary between the intermediate bonding layer 21 and the electrode layer 23 in a thickness of about several 10 Å, and the intermediate bonding layer 21 and the electrode layer 23 are thereby caused to be further tightly bonded to each other.

Figure 12C:
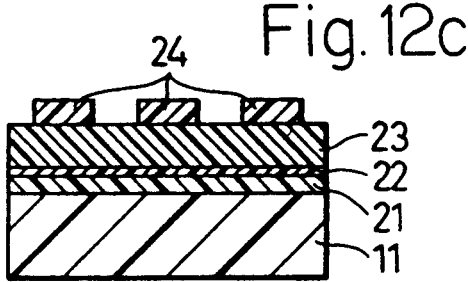
Figure 12D:
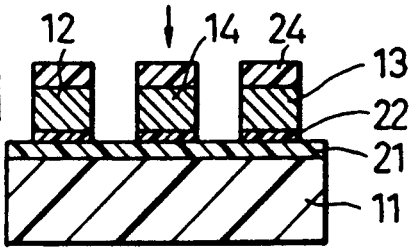
Figure 12B:
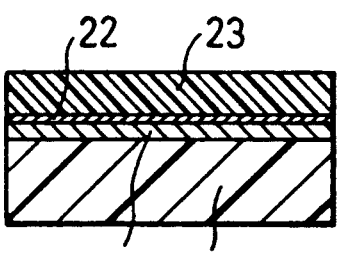
Figure 12E:
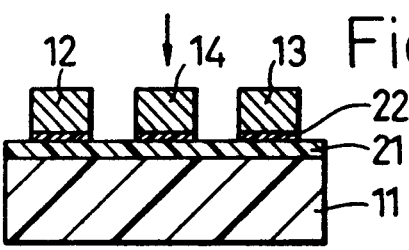
Figure 12F:
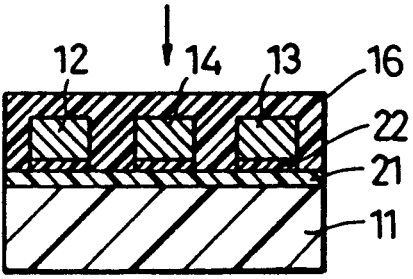

After an application of a photoresist on the electrode layer 23, the photoresist is subjected to a light exposure according to an ordinary photolithographic process and then to an etching process, and a photoresist layer 24 corresponding to the active, counter and reference electrodes 12-14 is formed, as seen in FIG. 12c. Next, this photoresist layer 24 is utilized as the mask, the respective electrodes 12-14 are formed from the electrode layer 23 through the etching process by means of an ion beam of argon, as shown in FIG. 12d. It is desirable that this processing is executed under conditions of an acceleration voltage of 800 V, an ion gun current of 600 mA, a beam incident angle of 0° and an etching time of about 20 minutes. Through this etching process, the metallic compound layer 22 is also processed concurrently. As shown in FIG. 12e, next, the photoresist layer 24 is removed and, thereafter, perfluorosulfonate polymer is made to heap up over the exposed intermediate bonding layer 21 and respective electrodes 12-14 by means of solution casting process and to set, finally, to thereby form the solid electrolyte layer 16, as shown in FIG. 12f.

While in the foregoing steps the electrode layer 23 has been referred to as being formed by Pt, such ordinary metallic materials as Ag, Ir and so on for use as the electrode may commonly be employed, and Au may be also used for the whole surface or a portion corresponding to the reference electrode. In forming the active, counter and reference electrodes 12, 13 and 14 through the etching process, it is possible to employ any of such dry etching as sputtering, plasma and the like etching, a wet etching and a combined etching of the dry and wet etchings. In forming the metallic compound layer 22, further, it may be possible to employ either a process of heaping up a material for forming the electrode layer 23 on the intermediate bonding layer 21 and then heat-processing the heaped up material at a temperature of about 300° C., or a process of causing the metallic compound of the electrode material and silicone to be heaped up by means of the sputtering or the like process on the intermediate bonding layer 21. The thickness of the metallic compound layer 22 may be achieved in a range of 10–1000 Å, but it is preferable that the thickness is smaller so long as the bonding strength is satisfactory. For the formation of the electrode layer 21 per se, a mask deposition or any planar techniques will be employable.

According to another feature of the present invention, there is taken a measure for increasing the effective surface area of the active and counter electrodes and improving the ion conductivity. Referring to FIGS. 13 and 14, the insulating substrate 11 is formed to have many upward projections 30, so that an electrode part 31 for forming the reactive portions 12a and 13a of the active and counter electrodes 12 and 13 will also have many projections 32 or, in other words, the whole surface of the electrode part 31 will be continuously projected and indented. Over the thus continuously projected and indented surface of the electrode part 31, a solid electrolyte layer 16a is provided in such that, as seen in FIG. 14 in particular, the layer 16a is made thick at indented part 33 between the respective projections 32 but is made thin on the projections 32 and on top and side faces of the projections 32. In this embodiment, the surface area of the electrode part 31 is enlarged and concurrently the area of electrochemical reaction with respect to the gas to be detected is expanded. The fact that the solid electrolyte layer 16a is thinner from the top surface to the side faces of the projections 32 causes not substantial deterioration in the permeability of molecules of the gas to be detected, whereas the thickly heaped up layer 16a in the indented part 33 between the projections 32 allows ions produced by the electrochemical reaction to smoothly shift through this thick zone of the layer 16a, whereby the ionic conductivity can be improved and the sensitivity to the gas can be effectively improved in accordance with the enlargement of the effective surface area of the electrode part 31.

The width and space of the respective projections 32 or the indented part 33 in the foregoing will not provide any desired function if they are excessively larger, and are desired to be set in a range of several $\mu$m to several 10 $\mu$m and to be 10 to 50 $\mu$m high. Since it has been found that major portion contributive to the electrochemical reaction in the electrode part 31 of the present embodiment is the side faces of the projections 32, it is required to pay attention to that, as will be appreciated, the presence of the thin area in the solid electrolyte 16b at the side faces of the projections 32 is assured, in order to increase the effective surface area of the electrode part 31 to the electrochemical reaction.

Now, sensitivity measurement has been carried out with respect to the gas sensor of FIG. 13, in which the width B of the projections 32 was made about 5 $\mu$m, the space S between the projections 32, that is, the width of the indented part 33 was about 5 $\mu$m, the height H of the projections 32 was about 50 $\mu$m, and film thickness of perfluorosulfonate polymer as the solid electrolyte layer 16b was about 10 $\mu$m at the indented part 33 and about 1 μm at portions from the side faces to the top faces of the projections 32, results of which were as shown in FIG. 15, and it has been found that the sensitivity has been remarkably improved as compared with that of the gas sensor having the solid electrolyte layer 16 about 10 μm thick formed on the reactive portions of the flat electrodes.

The sensitivity measurement has been also carried out with respect to a gas sensor of the same structure as the embodiment of FIGS. 13 and 14 except that the solid electrolyte layer 16b was formed only on the indented part 33 between the projections 32 as shown in FIG. 16, results of which were as shown in FIG. 17, and it has been found that, while the extent was less than that of the embodiment of FIGS. 13 and 14, the sensitivity could be optimumly improved more than in the case of the gas sensor having the solid electrolyte layer 16 about 10 μm thick on the reactive portions of the flat electrodes.

In carrying out the measurement for the gas sensors of FIGS. 13, 14 and FIG. 16, the CO gas of 1000 ppm was fed as the gas to be detected, ambient conditions were set to be at a temperature of 20° C. with a humidity of 60%, and the potential of the active electrode was set 0.40 V with respect to the reference electrode. Optimumly, the solid electrolyte layer is made to be more than 20 μm between the projections 32, and less than 5 μm at portions from the side faces to the top faces of the projections 32.

According to another feature of the present invention, the ionic conductivity of the solid electrolyte layer can be further improved. In the present instance, the ionic conduction member forming the solid electrolyte layer consists of a matrix of one or both of perfluorosulfonate polymer and perfluorosulfonic acid polymer, and at least one selected from a group consisting of inorganic acid, inorganic acid salt, organic acid and organic acid salt. More specifically, in the ion conduction member forming the solid electrolyte layer, the carrier ion should preferably be protons of small ion diameter and/or monovalent cations of alkaline metals, taking into consideration that the member is to be the solid electrolyte layer, while not required to be limited thereto. Further, these carrier ions may be contained in the ionic conduction member respectively alone or jointly together at any optional ratio. For the inorganic and organic acids, it is preferable to employ the one high in the ion dissociation when it is intended to increase the total amount of the carrier ions, but they are not required to be limited to strong or ultrastrong acid and the like.

For the inorganic acid, sulfuric acid, phosphoric acid, nitric acid and so on are preferable, while such acid as hydrochloric acid, chloric acid, perchloric acid, hydroiodic acid, hydrobromide, polyphosphoric acid or the like may also be employed, though not required to be limited thereto. These acids should preferably be added as an aqueous solution of about 1N, but not required to be limited to this. For the organic acid, on the other hand, sulfonic acid, sulfinic acid, carboxylic acid and their various substitution derivatives may be enumerated, though not limited thereto, and any general organic compound having in molecules more than one of acidic functional groups may properly be employed. For example, hydroxy acid, amino acid and the like, as well as organic polymers and copolymers of polyacrylic acid, polymethacrylic acid and the like may be effectively employed.

In the foregoing organic acids, it is desirable to employ, in particular, $C_nH_{2n+1}SO_3H$ (n being an integer more than 1), their substitution products by fluorine, $C_nF_{2n+1}SO_3H$, and $C_nH_pF_qSO_3H$ (p and q being 0 or an integer more than 1, and $p+q=2n+1$) or a copolymer of tetrafluoroethylene and perfluoro-3, 6-dioxa-4-methyl-7-octen-sulfonyl fluoride. These strong or ultrastrong acids are excellent in the compatibility with the polymers forming the matrix, without causing any phase separation, and show extremely remarkable effect of addition. More concretely, such ones available in the market and $n \leq 10$ in the foregoings as $CH_3SO_3H$, $CF_3SO_3H$, $C_2H_5SO_3H$, $C_2F_5SO_3H$, $C_4H_9SO_3H$, $C_4F_9SO_3H$, $C_5H_{11}SO_3H$, $C_5F_{11}SO_3H$ and so on.

When the ionic conduction member includes, as the carrier ion, such cation as alkaline metal ion and the like, it is desirable to employ inorganic and organic acid salt containing a cation of the same species as ionic species of the carrier ion, such as $M_2SO_4$, $M_3PO_4$, $MNO_3$, $MClO_4$, —COOM, —$SO_3M$ and the like (wherein M=Li, Na, K or the like). It is preferable to add, for example, Na salt to Na⁺ conduction member, Li salt to Li⁺ conduction member, whereby the carrier ions in the conduction member can be increased by an amount of the addition and the ionic conductivity can be thereby improved, though not required to be limited thereto. If desired, it is possible to concurrently employ a plurality of the acid salts or acids so as to attain a plurality of the carrier ions, in such combination as more than two different types of the organic acid salts, more than two different types of the inorganic acid salts, the inorganic acid with the organic acid, and the inorganic acid with the inorganic acid salt.

In respect of the adding amount of the foregoing inorganic and organic acids and inorganic and organic acid salts, it may be properly set in accordance with their type, or intended characteristics of the ionic conduction member. In an event where, for example, an inorganic acid is added as an aqueous solution of about 1N, it is proper that the acid is so added that its content will reach about 5 to 10 wt. % of the whole of the ionic conduction member being prepared. An excessively added amount of an aqueous solution of acid will be likely to cause cracks yielded during film formation by means of a casting or the like occasion, whereas an employment of a solid state organic acid or salt allows its adding amount to be increased until it reaches about 50 wt. % of the whole of the ionic conduction member.

As a raw material of the foregoing perfluorosulfonate polymer or perfluorosulfonic acid polymer, such NAFION by Du Pont as has been referred to may be used, though not limited thereto.

Referring further to steps in which the carrier ions form the solid electrolyte layer of proton, such a perfluorosulfonate polymer solution as the foregoing NAFION of the Na⁺ solution is placed in an evaporator, first, to have a solvent of the solution evaporated. The polymer in the solid state after the evaporation is then immersed in an aqueous solution of acid, for example, 1N sulfuric, hydrochloric or phosphoric acid solution. The thus immersed polymer is washed with distilled water and thereafter with a low grade solvent, and is then dissolved in a high grade solvent to obtain a polymer solution. Optional inorganic or organic acid is then added into and mixed with this polymer solution, such inorganic or organic acid containing polymer solution is cast over the reactive portions of the active and counter electrodes and dried, and the solid electrolyte layer as the proton conduction member is thereby completed.

For the low grade solvent, such low polarity solvent as toluene, xylene and the like may be employed desirably, but such polar solvent as acetone, tetrahydrofuran, dioxane, cellosolve and the like may also be employed so long as any slight flow-out of the polymer may be admitted. For the high grade solvent, alcohol, alcohol with water added and the like should preferably be employed, while methanol, ethanol, n-propanol (PA), isopropyl alcohol (IPA) and the like may also be utilized respectively alone or in a combination of two or more.

In preparing a cationic solid electrolyte layer in which the carrier ion is an alkaline metal ion=$M^+$ and the like, a perfluorosulfonate polymer solution in which counter ion is $M^+$ is prepared first, optional inorganic and organic acid salts having the same species cation ($M^+$) as the counter ion of the polymer are added to and mixed with the polymer solution, the thus mixed solution is then cast over the reactive portions of the active and counter electrodes, the cast solution is dried and the solid electrolyte layer is completed.

EXAMPLES 1-6

A sodium salt solution of perfluorosulfonate polymer, that is, NAFION of Du Pont of a resin concentration 5 wt. % with a solvent PA+IPA+water of 10 wt. % and equivalent weight (EW) of 1100 was used, and the solvent was made to volatilize under conditions of 50° C. and vacuum pressure of 10 Torr. A solid polymer here obtained was immersed in 1N sulfuric acid at 70° C. for an hour to carry out an ion exchange into proton, and this treatment was repeated further twice with the sulfuric acid renewed every time. The solid polymer thus treated was then subjected to a detergent treatment of being immersed in distilled water for 1 hour, the treatment was repeated three times and thereafter the polymer was dried. The thus obtained solid polymer was then dissolved in a mixed solution of PA:IPA=1:1 (weight ratio), and a perfluorosulfonic acid polymer solution of a resin content of 5 wt. % was obtained.

Such inorganic and organic acids as shown in following TABLE I were added respectively to the foregoing polymer solution to prepare different inorganic or organic acid containing polymer solutions for EXAMPLES 1 through 6. In this case, the added amount by wt. % in the above is a ratio with respect to the whole of the ionic conduction member prepared so that, for example, 4.76 wt. % would be polymer: inorganic or organic acid =100:5 and the each inorganic acid has been added in the form of 1N aqueous solution. Each of the polymer solutions thus obtained was cast over the reactive portions of the electrodes and dried, and a solid electrolyte layer as a proton ($H^+$) conduction member was obtained.

EXAMPLES 7-13

The solid polymer obtained with the same NAFION as in the foregoing EXAMPLES 1-6 and through the same treatments carried out was immersed for 1 hour in an aqueous solution at 70° C. and 5 wt. % of any one of lithium chloride, sodium chloride and potassium chloride to carry out the ion exchange to the cation, and this treatment was repeated further twice with the solution renewed every time, and a perfluorosulfonate polymer solution of a resin content of 5 wt. % was obtained in the same manner as in the foregoing EXAMPLES 1-6.

Such inorganic and organic acid salts as shown also in TABLE I were added respectively to the above polymer solution to prepare different inorganic or organic acid salt containing polymer solutions for EXAMPLES 7 through 13, each of these solutions was cast in the same manner as in the foregoing EXAMPLES 1 through 6, and a solid electrolyte layer as a $Li^+$, $Na^+$ or $K^+$ conduction member was obtained.

COMPARATIVE EXAMPLES 1-4

With polymer solutions not containing such inorganic and organic acids and inorganic and organic acid salts added as in the foregoing EXAMPLES 1 through 13 employed but treated in the same manner as in these examples, $H^+$, $Li^+$, $Na^+$ and $K^+$ conduction members were obtained.

Figure 18:
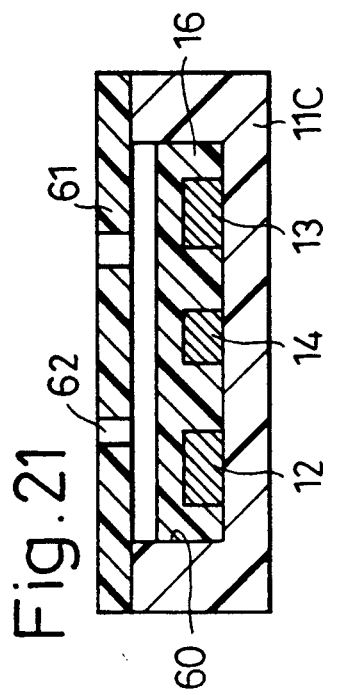
FIG. 18 is a schematic sectional view showing a state in which the impedance measurement is made with respect to an ionic conduction member employed in the sensor of the present invention.

The respective ionic conduction members of these EXAMPLES 1-13 and COMPARATIVE EXAMPLES 1-4 were subjected to impedance measurement in such manner as shown in FIG. 18. That is, on a deposited gold electrode 41 on a glass substrate 40, each of the ionic conduction members 42 of the EXAMPLES 1-16 and COMPARATIVE EXAMPLES 1-4 and an insulating resin layer 43 were jointly provided, a further deposited gold electrode 44 was stacked over the ionic conduction member 42 and insulating resin layer 43, and lead wires 45 and 45a were connected respectively to each of the gold electrodes 41 and 43. These lead wires 45 and 45a were connected to an LCR meter (not shown), and the measurement was carried out with the LCR meter set to be of a frequency of 1 KHz, biasing of 0.0 V and amplitude of 0.1 V.

TABLE I

| | Carrier | Additive | Added Amt. (wt. %) | Impedance ($\Omega \cdot cm$) |
|---|---|---|---|---|
| EX. 1 | $H^+$ | $H_2SO_4$ | 4.76 | $8.24 \times 10^4$ |
| EX. 2 | $H^+$ | $H_3PO_4$ | 4.76 | $1.59 \times 10^5$ |
| EX. 3 | $H^+$ | $HNO_3$ | 4.76 | $1.68 \times 10^5$ |
| EX. 4 | $H^+$ | $CF_3SO_3H$ | 4.76 | $7.68 \times 10^4$ |
| EX. 5 | $H^+$ | $C_2F_7SO_3H$ | 4.0 | $9.13 \times 10^4$ |
| EX. 6 | $H^+$ | $C_4F_9SO_3H$ | 4.0 | $9.42 \times 10^4$ |
| EX. 7 | $Li^+$ | $LiClO_4$ | 3.0 | $3.52 \times 10^6$ |
| EX. 8 | $Li^+$ | $LiSO_4$ | 3.0 | $3.29 \times 10^6$ |
| EX. 9 | $Na^+$ | $NaSO_4$ | 3.0 | $1.48 \times 10^7$ |
| EX. 10 | $K^+$ | $K_2SO_4$ | 3.0 | $4.89 \times 10^7$ |
| EX. 11 | $Li^+$ | $CF_3SO_3Li$ | 16.67 | $1.23 \times 10^6$ |
| EX. 12 | $Na^+$ | $CF_3SO_3Na$ | 16.67 | $9.25 \times 10^6$ |
| EX. 13 | $K^+$ | $C_4F_9SO_3K$ | 16.67 | $4.23 \times 10^7$ |
| COMP. EX. 1 | $H^+$ | — | — | $3.19 \times 10^5$ |
| COMP. EX. 2 | $Li^+$ | — | — | $5.22 \times 10^6$ |
| COMP. EX. 3 | $Na^+$ | — | — | $4.73 \times 10^7$ |
| COMP. EX. 4 | $K^+$ | — | — | $8.74 \times 10^7$ |

It has been found that, as will be clear from the above TABLE I, the respective solid electrolyte layers of EXAMPLES 1-13 which containing the acid or acid salt have been remarkably improved in the ionic conductivity in contrast to COMPARATIVE EXAMPLES 1-4.

According to another feature of the present invention, end hydroxyl group of polyethylene oxide employed as the matrix is etherificated, and a solid electrolyte layer as an ionic conduction member made higher in the conductivity can be provided. In the present instance, the solid electrolyte layer as the ionic conduction member is formed by polyethylene oxide of a molecular weight of 10,000 and above, polyethylene oxide of a molecular weight less than 10,000 and an alkaline metallic salt of perfluorohydrocarbon sulfonate. In this case, the conductivity can be improved by the metallic salt of perfluorohydrocarbon sulfonate which is an ultrastrong acid salt.

EXAMPLE 14

A solution was prepared with a composition of polyethylene glycol of 1.0 wt. %, tetraethylene glycol of 1.0 wt. %, trifluoromethane sulfonate lithium salt of 0.4 wt. % and distilled water of 97.6 wt. %, the solution was cast over the reactive portions of the active and counter electrodes and dried, and a solid electrolyte layer of a lithium conduction member 10–30 μm thick was obtained.

EXAMPLE 15

A solution was prepared with a composition of polyethylene glycol of 1.0 wt. %, tetraethylene glycol of 1.0 wt. %, nonafluorobutane sulfonate lithium salt of 0.5 wt. % and distilled water of 97.5 wt. %, and a solid electrolyte layer was obtained in the same manner as in EXAMPLE 14.

EXAMPLE 16

A solid electrolyte layer was obtained in the same manner as in EXAMPLE 14 except for a use of trifluoromethane sulfonate sodium salt in place of trifluoromethane sulfonate lithium salt of EXAMPLE 14.

EXAMPLE 17

A solid electrolyte layer was obtained in the same manner as in EXAMPLE 15 except for a use of trifluoromethane sulfonate lithium salt instead of nonafluorobutane sulfonate lithium salt of EXAMPLE 15.

The respective solid electrolyte layers of the above EXAMPLES 14–17 were subjected to the impedance measurement carried out in the same manner as in FIG. 18, and it has been found that these solid electrolyte layers have obtained such excellent ionic conductivity that, at 1 KHz, $6.2\times 10^4$ (Ω.cm) for the layer of EXAMPLE 14, $8.6\times 10^5$ (Ω.cm) for the one of EXAMPLE 15, $4.7\times 10^6$ (Ω.cm) for the one of EXAMPLE 16, and $1.2\times 10^4$ (Ω.cm) for the one of EXAMPLE 17.

Figure 19:
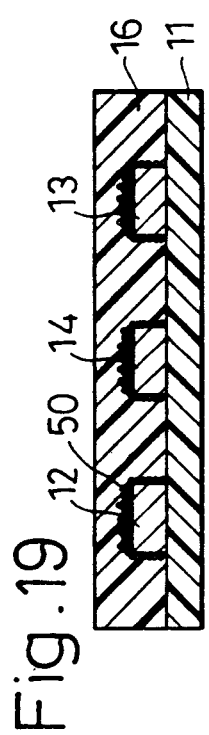
FIG. 19 is a fragmentary sectional view of another embodiment of the present invention.
Figure 20:
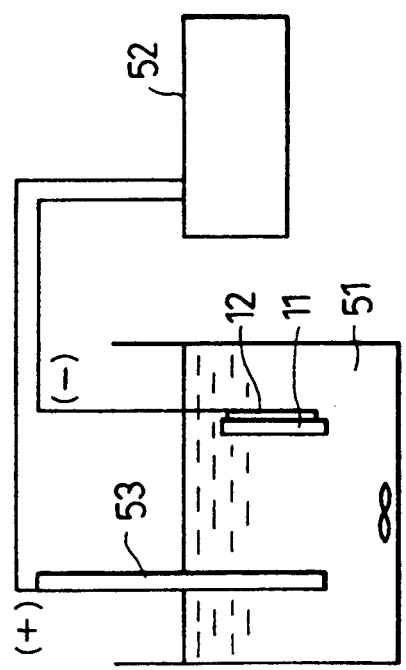
FIG. 20 is an explanatory view for the manufacture of the sensor in FIG. 19.

According to still another feature of the present invention, the reactive portions of at least the active electrode among the three electrodes are covered by fine particle member, so that the reactive surface area will be thereby increased. Referring to FIG. 19, respective surfaces of the active, counter and reference electrodes 12–14 formed on one surface of the insulating substrate 11 are covered by fine particles 50 of an electrically conducting material, and they are all embedded in the solid electrolyte layer 16. In this case, it is not always required that the counter and reference electrodes 13 and 14 are covered by the fine particles 50. In covering the reactive portions of such electrodes as the active electrode 12 and so on with the fine particles, as shown for example in FIG. 20, a bath 51 of platinum chloride aqueous solution is prepared, the insulating substrate 11 carrying the active electrode 12 and so on is immersed in this bath 51 and connected on the side of the electrode to cathode side of a galvanostat 52, and a platinum plate 53 is connected to anode side of the galvanostat 52 and immersed in the bath 51. In this state, a constant current is made by the galvanostat 52 to flow between the active electrode 12 and so on and the platinum plate 53, and fine platinum particles separating out of the platinum plate 53 can be made to adhere onto the surface of the active electrode 12 and so on.

According to yet another feature of the present invention, the gas detection sensitivity can be prevented from being rapidly deteriorated due to variation with time. In this case, it will be appreciated that the detection current Is in the electrochemical gas sensor is represented by $$Is = nFADC/\delta$$

[wherein n being the number of electrons, F being Faraday constant (96,500 c/mol), A being the size of gas diffusion surface (cm$^2$), D being the gas diffusion coefficient (cm$^2$/s), δ being the thickness of diffusion layer, and C being the gas concentration (mol)], and that this detection current is influenced not only by the gas concentration C but also by the size (cm$^2$) of the gas diffusion surface. Therefore, the concentration cannot be accurately detected any more when the solid state properties of the solid electrolyte which are directly concerned to the diffusion coefficient are caused to vary due to some factors. As one of such factors that cause the properties to vary with time, a participation of air stream moving toward the gas sensor detecting surface is remarkable. In view of this respect, there is provided an overlayer, according to the present invention.

Figure 21:
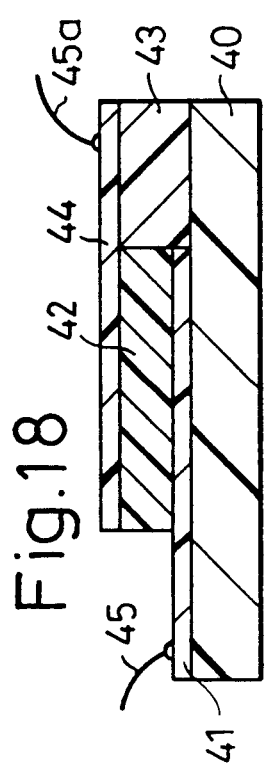
FIG. 21 shows in a sectional view another embodiment according to the present invention.

Referring more specifically to this by references to FIG. 21, an insulating substrate 11c in this embodiment is formed preferably to have a recess 60, the active electrode 12, counter electrode 13 and reference electrode 14 are provided on the bottom of this recess 60, and the solid electrolyte layer 16 is provided to cover the reactive portions of these electrodes within the recess. Further, an overlayer 61 having a plurality of small ventilating holes 62 is provided to cover the recess 60 but separated from the solid electrolyte layer 16 to leave a space thereabove.

Figure 22:
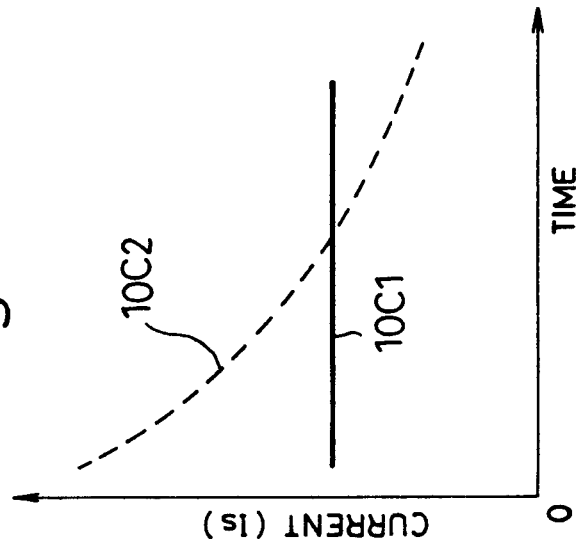
FIG. 22 is a diagram for explaining the operation of the sensor of FIG. 21.

The overlayer 61 is formed by a gas barrier material, for example, such synthetic resin as an acrylic resin and the like or a glass material, but is provided with some extent of gas permeability by means of the small ventilating holes 62. It is also possible to form this overlayer 61 with any other material that shows the gas barrier property and also the gas permeability to some extent, such as an inorganic porous member, porous polymer and the like. Here, the variation with time of the detection sensitivity has been measured with respect to the gas sensor of, for example, FIG. 1 the detection surface of which is exposed and to the gas sensor of the present embodiment of FIG. 21, and it has been found that, while the sensitivity of the sensor with the exposed detection surface is quickly deteriorated as time lapses, as shown by a curve 10C2 in FIG. 22, the sensitivity of the sensor having the overlayer 61 involves no variation with time and in substantially constant, as represented by a curve 10C1 in FIG. 22.

Figure 23A:
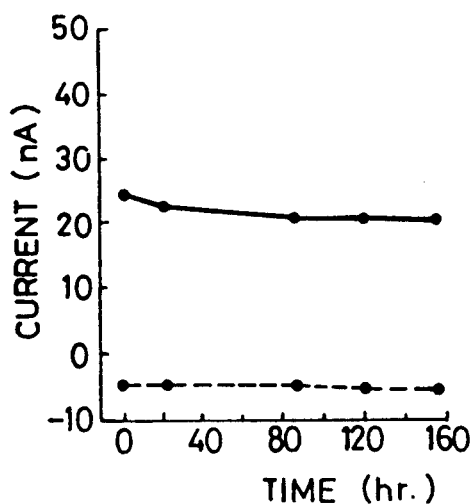
FIGS. 23a through 23d are graphs showing variation in time of the sensor in FIG. 21.
Figure 23B:
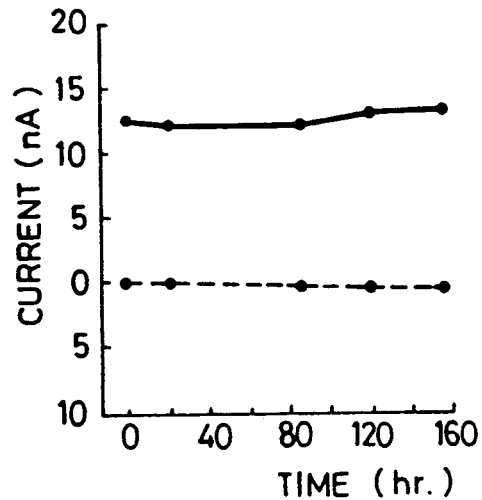
Figure 23C:
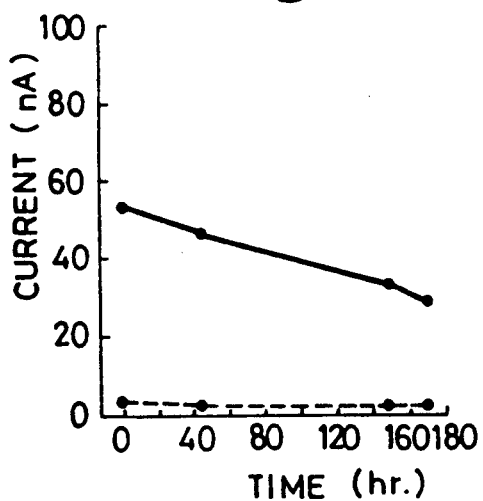
Figure 23D:
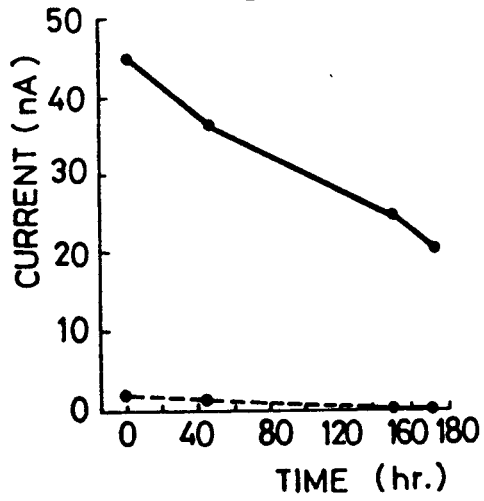

More specifically, the variation with time of the detection sensitivity was investigated in respect of the gas sensors of the arrangement of FIG. 21 but with the number of the small ventilating holes 62 made to be 0.3 mmφ in an acrylic plate of 1 mm thick as the overlayer 61 was varied to be four, one and 10, and of the gas sensor having the exposed detection surface. In carrying out this investigation, CO gas of 1,000 ppm was fed into an atmosphere at a temperature of 20° C. and RH 60%, and a voltage of 0.40 V was applied across the active and reference electrodes 12 and 14. Resultant measurement for the respective sensors was as in FIG. 23a for the one having four ventilating holes 62, in FIG. 23b for the one having only one hole 62, in FIG. 23c for the one of ten holes 62, and in FIG. 23d for the one of the exposed detection surface, while in these drawings the dark current was as shown by a dotted line curves. From these results diagraphically shown, it will be appreciated that the gas sensor of FIG. 21 where the ventilating hole 62 is made to be four and one shows substantially no deteriorative variation with time in the detection current as will be clear when FIGS. 23a and 23b are compared with FIG. 23d of the sensor of FIG. 1 of the exposed detection surface. In the case where the ventilating hole 62 was made ten, on the other hand, it has been found that the gas permeation was excessive enough for causing the detection current varied to decrease with time, and that the ventilating hole number was improper for restraining the variation with time to stabilize the sensitivity. Here, the surface area of the overlayer 61 was 7×7 cm.

Figure 24:
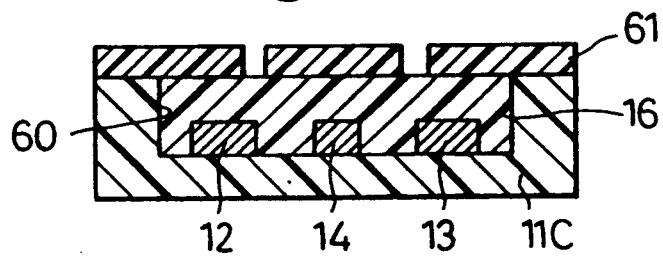
FIG. 24 shows in a sectional view another embodiment according to the present invention.
Figure 25:
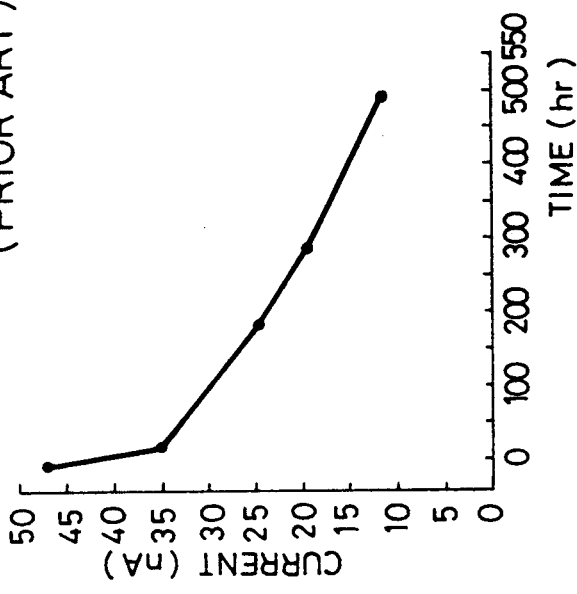
FIG. 25 is a graph showing a detection current responsive to the CO gas inflow time in the sensor of FIG. 24 in the presence of ventilation.
Figure 26:
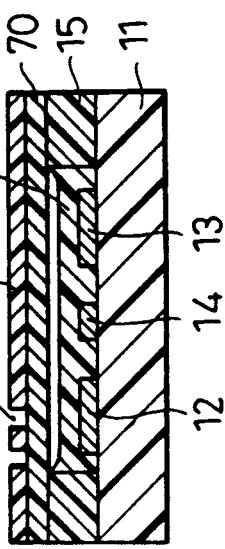
FIG. 26 is a graph showing a detection current responsive to the CO gas inflow time in a known sensor in the presence of ventilation.

Further, the sensitivity variation with time can be likewise restrained to some extent even when the overlayer 61 formed in the same manner as in the embodiment of FIG. 21 is disposed to be in contact with the solid electrolyte layer 16, as shown in FIG. 24. The sensitivity variation with time was measured for this sensor of FIG. 24 provided with the overlayer 61 having four ventilating holes 62 under the same conditions as in the case of FIG. 21, and results were as shown in FIG. 25. As will be clear when FIG. 25 of this measurement with FIG. 26 showing similar results of the measurement for the same gas sensor having the exposed detection surface as in FIG. 24d but with the measurement carried out for a longer time, it should be appreciated that this embodiment is also effective to improve the gas sensor in respect of the variation with time.

According to another feature of the present invention, there can be provided an electrochemical gas sensor having a selectivity for the objective gas to be detected. Referring thereto in detail with reference to FIG. 27, in this embodiment, a filter 70 permeable to a selective gas is provided to cover the frame 15 fitted peripherally to the insulating substrate 11 on which the active, counter and reference electrodes 12, 13 and 14 are provided as covered with the solid electrolyte layer 16. The filter 70 should preferably be separated from the solid electrolyte layer 16, but they may be brought into contact with each other. The filter 70 is formed by a material selected to be one permeable to the objective gas to be detected but restrainable for any other gas than the selected one and hindering its detection, and such material as a metallic oxide, ceramics, synthetic resin, synthetic fiber or the like may be properly employed in accordance with a composition of the gas to be restrained from passing. Further, the filter 70 may be formed either in a single layer or in a stack of a plurality of layers. It is also preferable that the filter 70 is formed by a porous member so as to render passing resistance of the gas to be detected while maintaining a large adsorptive surface area with respect to the gas to be restrained.

It has been found that, in circumstances where the electrochemical gas sensor is employed, for example, as a household gas-leakage or incomplete combustion sensor with CO and $H_2$ gases made as the object to be detected while the presence of ethanol and $NO_x$ gases is supposed, a porous member of an active alumina ($Al_2O_3$) is useful as the material for the filter 70. This active alumina porous member shows a nature highly permeable to the CO and $H_2$ gases but impermeable to either the ethanol gas which is physically adsorbed or the $NO_x$ gas which is chemically adsorbed. In the case of home kitchen, the ethanol gas is generated just transiently upon cooking and the physical adsorption is sufficient while the $NO_x$ gas high in the possibility of being generated gradually from combustion equipments should desirably be chemically adsorbed.

Figure 27:
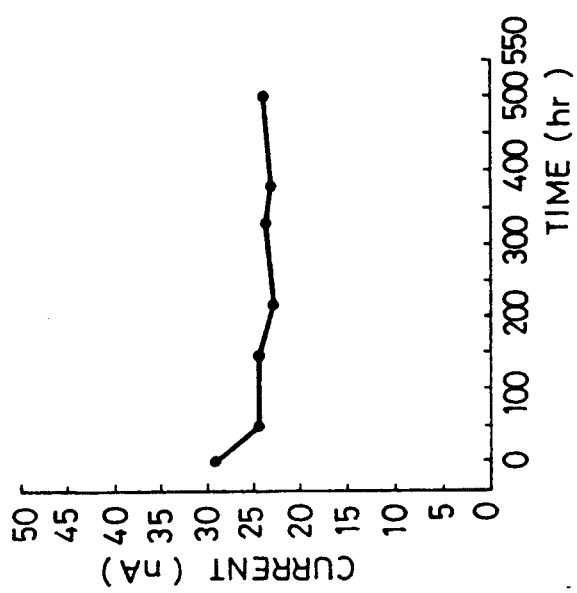
FIG. 27 shows in a sectional view another embodiment of the present invention.
Figure 28:
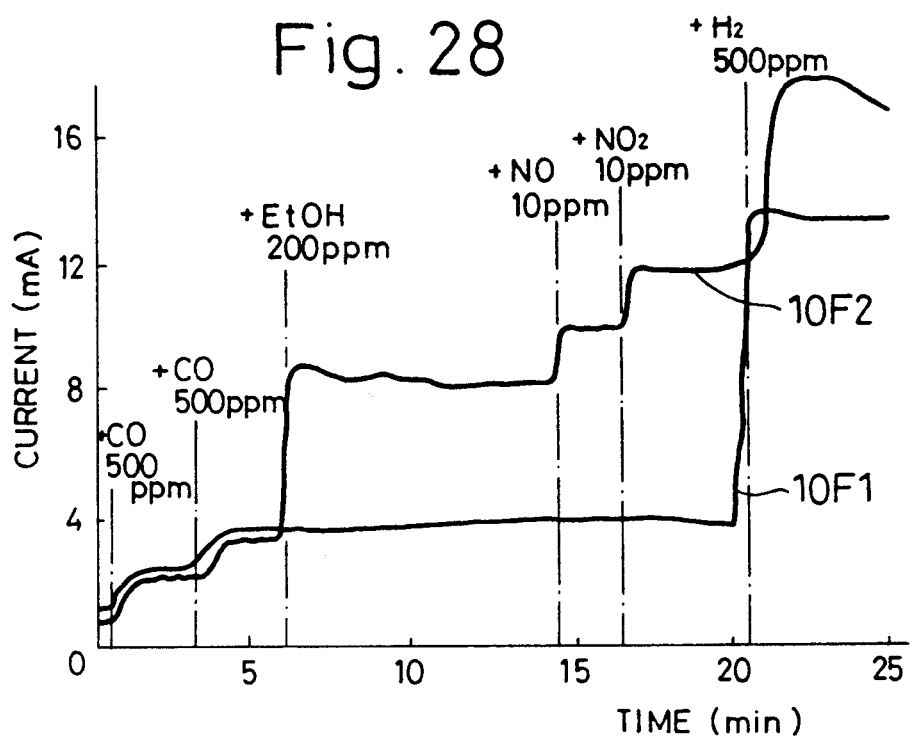
FIG. 28 is a graph showing detection currents responsive to the inflow time of CO, EtOH, NO, $NO_2$ and $H_2$ gases respectively sequentially fed to the sensor of FIG. 27.

A performance test has been carried out with respect to a gas sensor provided with the selective gas permeable filter formed by the foregoing active alumina porous member. In the test, an active alumina molded product by a Japanese firm SUMITOMO ALUMINIUM SEIREN K. K. of an apparent specific gravity 1.35 $g/cm^3$ and a macropore area 0.11 $cm^2/g$ was used as the filter material, the filter 70 was thereby formed and provided to such a gas sensor as shown in FIG. 27. To this gas sensor, the CO, EtOH, NO, $NO_2$ and $H_2$ gases were sequentially supplied, detected currents were measured, and its results were as shown diagrammatically in FIG. 28, in which drawing the measured results of the sensor provided with the filter 70 are represented by a curve 10F1 and, as will be clear when compared with a curve 10F2 showing measured results of a sensor not provided with any filter, the gas sensor according to the present invention causes the detected current responsive to supplied amount of the CO and $H_2$ gases to flow whereas the sensor has shown no reaction at all to the ethanol or $NO_x$ gas.

Figure 29:
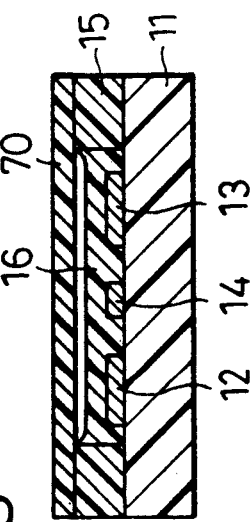
FIG. 29 shows in a sectional view another embodiment of the present invention.
Figure 30:
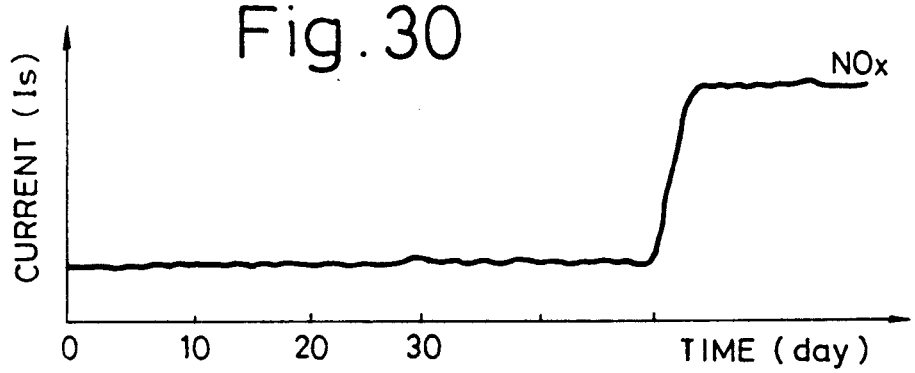
FIG. 30 is a graph showing a detection current responsive to elapsed days in the sensor of FIG. 29.
Figure 31:
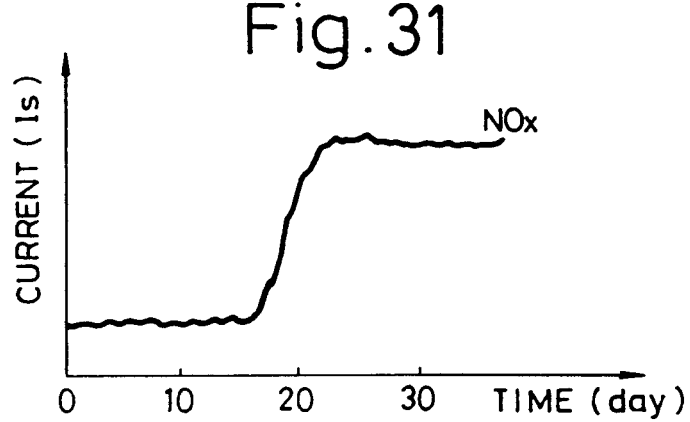
FIG. 31 is a graph showing a detection current when no passing-gas reduction cover member is employed in the sensor of FIG. 29 in response to the elapsed days.

Further on the filter 70, as shown in FIG. 29, such overlayer 61G as shown in the embodiment of FIG. 21 is stacked, whereby such variation with time as has been referred to in the above with reference to the gas sensor of FIG. 21 can be restrained. In this case, the small ventilating holes 62 provided in the overlayer 61G are desirably provided to be positioned right above the active electrode 12 since the gas permeation amount shows a tendency of being further restrained by the presence of the filter 70 to restrain the variation with time but the sensibility may happen to be made excessively low. It has been found that, as will be clear from a comparison of FIG. 30 showing the output measurement for such sensor as shown in FIG. 29 having the overlayer 61G and maintained in an NO atmosphere of 200 ppm, with FIG. 31 showing a similar output measurement of such sensor as in FIG. 27 having no overlayer, the sensor of FIG. 29 has operated effectively for about 50 days and is capable of stabilizing the variation with time.

According to still another feature of the present invention, the adhesiveness between the respective active, counter and reference electrodes and the solid electrolyte layer can be elevated and the electrochemical gas sensor can be improved in the durability. Referring to FIG. 32, in the present embodiment, an adhesiveness elevating layer 80 is provided within the frame 15 so as to cover at least the reactive portions of the respective active, counter and reference electrodes 12, 13 and 14 provided on the insulating substrate 11, and the solid electrolyte layer 16 is provided over the adhesiveness elevating layer 80. It is possible to provide this adhesiveness elevating layer 80 as a layer formed by, for example, a hydrophobic material so that a generation of any excessive water film between the electrodes and the hydrophobic layer can be prevented by the hydrophobic layer, and the adhesiveness between the electrodes and the solid electrolyte layer can be improved.

As the hydrophobic material, fluorine or silicone plastics may be enumerated. For the fluorine plastics, polyvinyl fluoride, polyvinylidene fluoride, polychlorotrifluoroethylene, polytetrafluoroethylene, ethylene-propylene copolymer fluoride, ethylene-tetrafluoroethylene copolymer, ethylene-chlorotrifluoroethylene copolymer, tetrafluoroethylene-perfluoroalkylvinylether copolymer, polyperfluorofuran and the like can be employed. Further, such modified resin of the above resins as alkyd modified, acrylic modified, polyester modified, phenol modified, melamine modified, urethane modified or the like resin can be employed. For the silicone plastics, on the other hand, silane or siloxane derivatives are preferable. For the one curable, preferable is the one consisting as main ingredients of, for example, $\alpha$, $\omega$-dihydroxydimethyl-polysiloxane or its derivative and polyfunctional silane or siloxane or its derivative. These ingredients may be the one cross-linked and, for the crosslinking method, acetic acid type, oxime type, alcohol type, amine type, amide type, acetone type, mastic type or the like method may be enumerated.

In forming the hydrophobic layer as the adhesiveness elevating layer, powder baking, deposition of low-molecular-weight material, casting of solution or dispersion, sputtering, plasma polymerization or the like process may be employed. Further, the hydrophobic layer should preferably be made thin and desirably to be less than 10 nm.

For the hydrophobic layer, other than the resins, on the other hand, a carbon layer of a thickness of 10–100 Å may be formed by means of, for example, a vacuum deposition.

Further, the adhesiveness elevating layer can be arranged by other member than the hydrophobic layer. That is, in the arrangement shown in FIG. 33, an adhesiveness elevating layer 80A is formed by carrying out a plasma processing with respect to a surface of the insulating substrate 11 on which the active, counter and reference electrodes 12, 13 and 14 are provided. In this event, radicals are produced on the surface of the substrate 11 and on the respective electrodes and, when the solid electrolyte layer 16 is formed in this state, a chemical coupling occurs between the insulating substrate 11 and the respective electrodes to cause the adhesiveness improved. As shown in FIG. 34, further, an impermeable layer 80B is formed on outer surface of the solid electrolyte layer 16, so as to prevent any moisture within the solid electrolyte layer 16 from escaping to the exterior and to restrict any diffusion of external CO gas into the solid electrolyte layer 16. While the impermeable layer 80B is less permeable to the moisture, the layer functions to allow a fixed amount of the objective gas to be detected to permeate therethrough to the solid electrolyte layer 16. As shown in FIG. 35, further, it is also possible to provide concurrently the adhesiveness elevating layer 80 on boundary plane between the electrodes and the solid electrolyte layer and the impermeable layer 80B on top surface of the electrolyte layer 16.

The foregoing hydrophobic, plasma processed and impermeable layers are formed in such a thickness or by such a material that allows ingredients of the objective gas to be detected to permeate therethrough and, from this viewpoint, a fluoropolymer or a hydrocarbon polymer, for example, is employed for the impermeable layer. For the fluoropolymer, the material for use in forming the hydrophobic layer may be employed and, for the hydrocarbon polymer, polyethylene, polypropylene, polybutene, polymethylpentene and the like and modified resins of these resins, that is, alkyd modified, epoxy modified, acrylic modified, polyester modified, phenol modified, melamine modified, urethane modified and the like modified resins can be employed.

According to still another feature of the present invention, there can be provided an electrochemical gas sensor in which the moisture content of the solid electrolyte layer is maintained substantially constant so as to render the dependence on the moisture to be less and to function excellently and stably in a wide moisture range. Referring to FIG. 36, the insulating substrate 11 on which the active, counter and reference electrodes 12–14 are provided and covered by the solid electrolyte layer 16 provided inside the frame 15 is further mounted on a reservoir casing 90, in this embodiment. The reservoir casing 90 comprises a storing chamber 91 in which water is sealed (water may be encased as retained in a water-absorbing polymer) while a wick 92 is immersed at its one end in the stored water in the chamber 91 and bonded at the other end led out of the casing to top surface of the solid electrolyte layer 16. The wick 92 itself is formed by a water-absorbing fiber member so that water will be provided from the storing chamber 91 to the solid electrolyte layer 16 with the capillarity utilized. Even in an event where the moisture in the solid electrolyte layer 16 is caused to evaporate due to a decrement in ambient moisture at the location where the gas sensor is used, therefore, the layer 16 is immediately supplied with moisture to maintain a proper moisture in the solid electrolyte layer 16 for an excellent execution of ionic conduction. Further, electric resistance influenced by the water content in the solid electrolyte layer 16 is also stabilized, and in general the sensitivity of the gas sensor can be maintained constant.

Referring to FIG. 37, there is provided in this embodiment an arrangement capable of supplying water to the solid electrolyte layer 16 without using the wick. That is, in a storing chamber 91A, a communicating path 93 reaching bottom surface of the insulating substrate 11 is formed, and a water supply hole 94 is made in the insulating substrate 11 for communication between the communicating path 93 and the solid electrolyte layer 16, whereby water can be properly supplied through the communicating path 93 and water supply hole 94 to the layer 16 in an event of the moisture evaporation at the solid electrolyte layer 16. In the present instance, the storing chamber 91A from which the communicating path 93 extends is formed at its reservoir casing 90A in an annular shape, but may be provided to be positioned only on one side of the insulating substrate 11.

In the embodiments of FIGS. 36 and 37, the respective electrodes are shown to be flat, but it is preferable to employ such arrangement as has been referred to with reference to FIG. 13, 14 or 16 so that the active and counter electrodes 12 and 13 are provided as made uneven as shown in FIG. 38.

Figure 39:
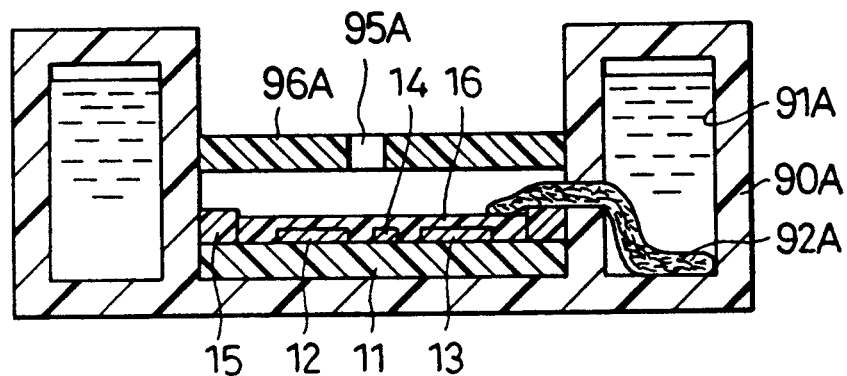

In addition to such moisture supply arrangement as has been referred to for the solid electrolyte layer 16, it is possible to concurrently provide the overlayer shown in FIG. 21 so that the overlayer will control any influence of air stream on the detecting surface of the sensor, so as to be contributive to the sensor sensitivity stabilization and to be capable of preventing the moisture in the solid electrolyte layer 16 from being lowered. Referring to FIG. 39, the reservoir casing 90A is formed in this embodiment to define the annular storing chamber 91A, and the wick 92A dipped at one end in water of the storing chamber 91A is bonded at the other end to the surface of the solid electrolyte layer 16 provided to cover the insulating substrate 11 and the electrodes. With respect to the reservoir casing 90A, an overlayer 96A having a small ventilating hole 95A is provided to be above the solid electrolyte layer 16 as separated therefrom. With this arrangement, the moisture supply to the solid electrolyte layer 16 is performed through the wick 92A while ventilation amount with respect to the solid electrolyte layer 16 is controlled by the overlayer 96A, so that the evaporation can be restrained and the moisture content of the solid electrolyte layer 16 can be held at a level of stabilizing the electric resistance. No doubt, the sensor sensitivity can also be prevented from being rapidly lowered by the control of the air stream influence on the detecting surface of the sensor, as has been referred to with reference to the embodiment of FIG. 21.

Figure 40:
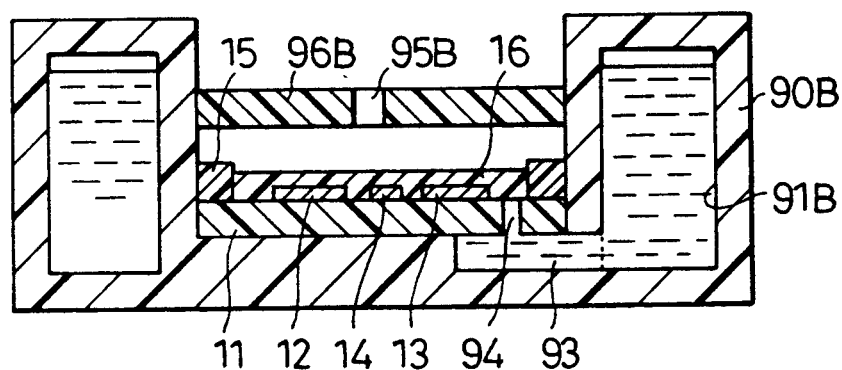
Figure 41:
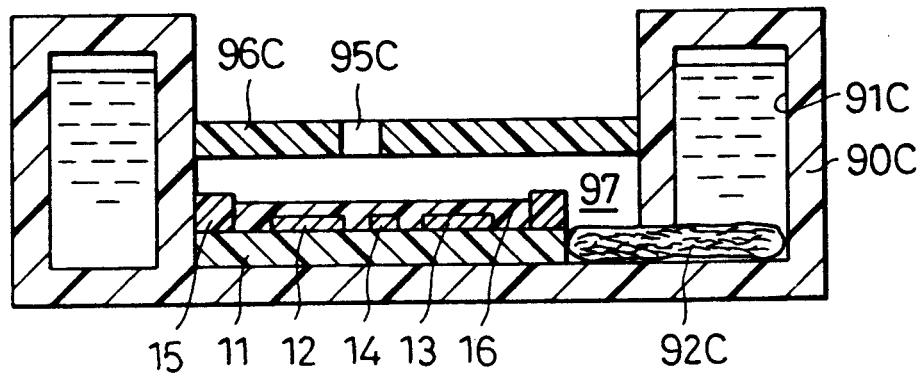

In an embodiment shown in FIG. 40, the electrochemical gas sensor shown in FIG. 37 is provided with an overlayer 96B having a small ventilating hole 95B and, in addition to the function referred to in the above with reference to FIG. 37, a stabilization of the moisture content is promoted. In another embodiment shown in FIG. 41, a reservoir casing 90C defines an annular storing chamber 91C, the insulating substrate 11 is disposed in the center of the reservoir casing 90C with a space 97 retained, and a wick 92C dipped at an end in the storing chamber 91C is disposed at the other end in the space. Further, an overlayer 96C having a small ventilating hole 95C is disposed as separated from the solid electrolyte layer 16 provided to cover the insulating substrate 11 and the electrodes. In this instance, the solid electrolyte layer 16 is not supplied with the moisture directly through the wick 92C, but the ambient moisture of the solid electrolyte layer 16 is elevated by disposing the other end of the wick 92 in the space 97 and the solid electrolyte layer 16 is to be indirectly moistened. At this time, the overlayer 96C prevents the moisture of the solid electrolyte layer 16 from evaporating and can be additionally contributive to the elevation of the ambient moisture of the layer 16 since it almost closes upper side of the layer 16.

Figure 42:
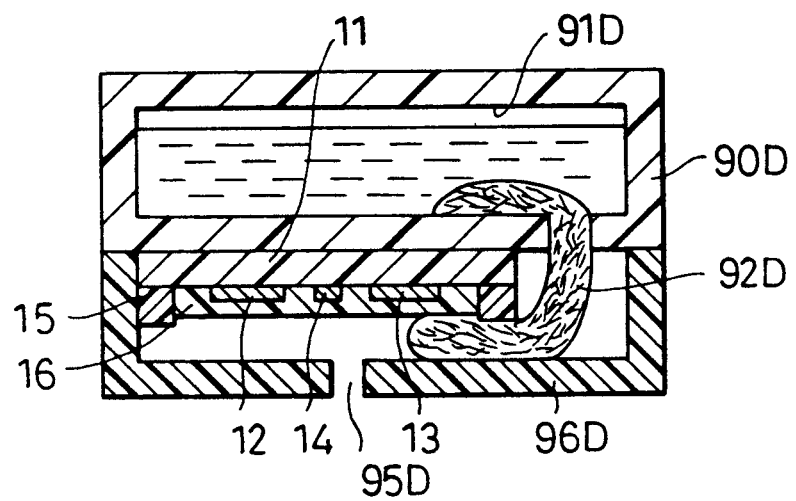

According to still another feature of the present invention, an electrochemical gas sensor which prevents the small ventilating hole of the overlayer from clogging is provided. Referring to FIG. 42, the insulating substrate 11 provided with the active, counter and reference electrodes 12-14 and the solid electrolyte layer 16 covering the respective electrodes inside the frame 15 is disposed in the present embodiment to be on upper side, and a reservoir casing 90D having a storing chamber 91D is provided above the substrate 11. Further, a wick 92D dipped at an end in the storing chamber 91D is bonded at the other end to the solid electrolyte layer 16, and they are covered by an overlayer 96D having a small ventilating hole 95D opened downward. In the present embodiment, in addition to that the same function as in the sensor of, for example, FIG. 39 can be attained, it is possible to prevent any oil mist or powdery dust from being deposited in the small ventilating hole 95D since the same is directed downward.

Figure 43:
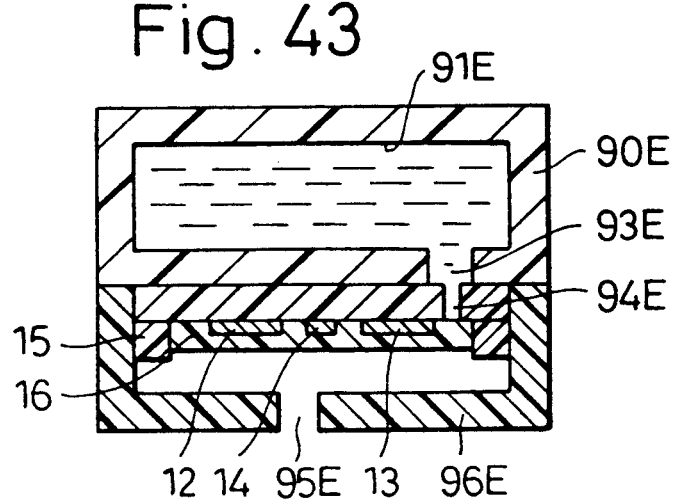

Another embodiment shown in FIG. 43 is of a structure in which the sensor in the embodiment of FIG. 40 is substantially turned upside down so as to be equivalent in the functions while different in that a storing chamber 91E simply rectangular in section is provided in contrast to the annular storing chamber in the sensor of the embodiment of FIG. 40, and substantially identical constituents to those in FIG. 40 are denoted with suffixes "A" in FIG. 40 altered to "B". In the present embodiment, the clogging prevention for small ventilation hole 95E can be realized in addition to the functions referred to in the above with reference to FIG. 40.

In another embodiment shown in FIG. 44, a plurality of holes 93F are provided in lower wall of a reservoir casing 90F having a storing chamber 91F, the holes being small enough for not causing water in the storing chamber 91F to drop, an overlayer 96F having a small ventilation hole 95F is provided to cover the lower wall of the casing 90F, and the insulating substrate 11 on which the active, counter and reference electrodes 12 to 14 are provided as covered by the solid electrolyte layer 16 is secured onto inner bottom face of the overlayer 96F. In the present embodiment, water in the storing chamber 91F is normally present in the small holes 93F to reach their outlet openings with the capillarity so that, as the moisture inside the overlayer 96F decreases, water that has reached the outlet openings of the small holes 93F will evaporate so as to maintain the interior of the overlayer 96F always at a high humidity, whereby the water content of the solid electrolyte layer 16 is retained to be optimum and the small ventilation hole 95F can be prevented from being clogged by any oil mist or powdery dust.

While the respective electrodes have been shown to be flat in the embodiments of FIGS. 42, 43 and 44, it is preferable to adopt the arrangement disclosed with reference to FIG. 13, 14 or 16 so as to form the active and counter electrodes 12 and 13 uneven as directed reverse to the case of FIG. 38, as shown in FIG. 45.

Figure 46:
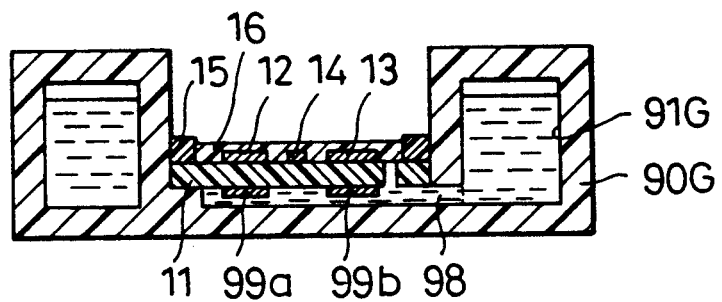

According to a still further feature of the present invention, there is additionally provided an arrangement for detecting the presence or absence of water in the storing chamber. Referring to FIG. 46, a communication path 98 is provided at bottom portion of a storing chamber 91G defined in a reservoir casing 90G in the present embodiment, and this communication path 98 reaches the bottom part of the insulating substrate 11. On the bottom part of the insulating substrate 11, a pair of detecting electrodes 99a and 99b are provided so that the detecting electrodes 99a and 99b will be mutually non-conductive when water is absent in the storing chamber 91G and the water absence can be notified when a notifying means is connected to these detecting electrodes 99a and 99b. Further, a provision of a port (not shown) for supplying water from the exterior to the storing chamber 91G allows a proper water replenishment realized. In providing the detecting electrodes 99a and 99b to the bottom wall of the insulating substrate 11, it is possible to employ the same material as that for the respective electrodes 12-14 and to adopt the same process for their provision.

Figure 47:
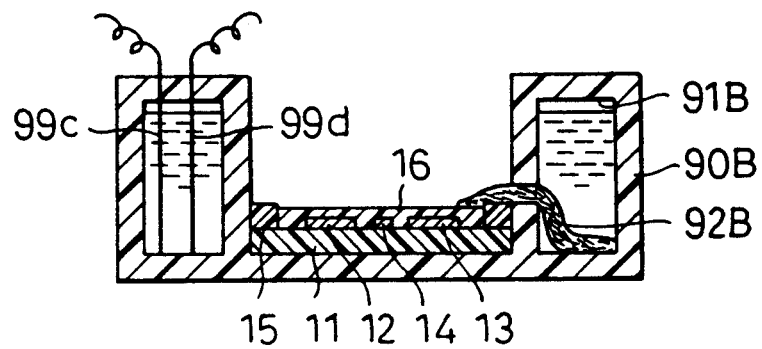
Figure 48:
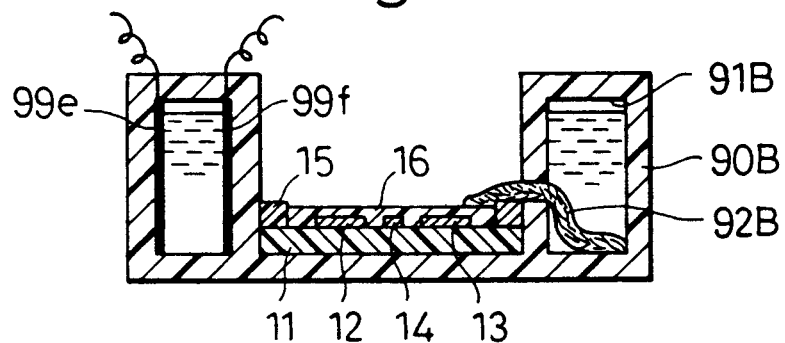
Figure 49:
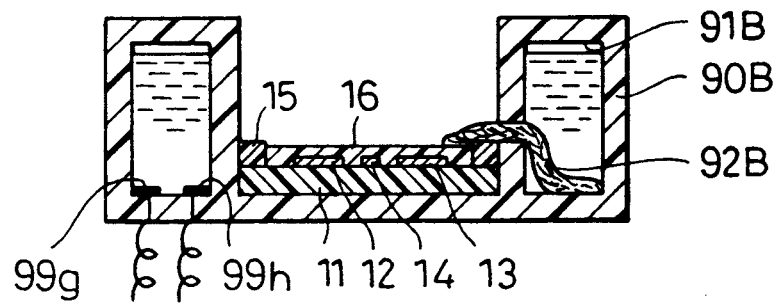

In an embodiment shown in FIG. 47, electrode bars 99c and 99d made of such electrode material as Au, Pt or the like are inserted in the storing chamber 91B of the reservoir casing 90B in an arrangement of the gas sensor in the embodiment shown in FIG. 39 from which the overlayer 96 is removed. In this sensor, too, the same function as that in the sensor shown in FIG. 46 can be attained. In the present instance, the electrode material of Au, Pt or the like may be deposited through the sputtering process to side walls of the storing chamber 91B as shown in FIG. 48 to from electrodes 99e and 99f, or the Au, Pt or such electrodes 99g and 99h as shown in FIG. 49 may be provided by depositing the Au, Pt or the like material through the sputtering process onto bottom surface of the storing chamber 91B.

Across the detecting electrodes of FIGS. 46-49, a voltage of, for example, 10-100 mv is to be applied.

According to yet another feature of the present invention, a water retention arrangement can be taken for the solid electrolyte layer 16. Referring to FIG. 50, a water retention layer 100 is provided over the solid electrolyte layer 16 covering the active, counter and reference electrodes 12-14 provided on the insulating substrate 11. This water retention layer 100 is formed by applying to surface area of the solid electrolyte layer 16 a gelatinous substance obtained by, for example, dissolving NAFION in ethanol and adding thereto $H_2SO_4$ by an amount of about 30-40 wt. % with respect to 100 wt. % of solid NAFION. Alternatively, the water retention layer 100 may be formed by employing a starch-/polyacrylic acid resin gelatinous substance or such hydrophilic polymer as polyvinyl pyrrolidone, polyvinyl alcohol, hyaluronic acid or the like.

In forming the water retention layer 100, further, it is necessary to maintain the permeability to gas to be excellent and various arrangements are provided. In an aspect of FIG. 51a, a plurality of permeation holes 101 are formed in the water retention layer 100A at its portion disposed above the active electrode 12 provide the permeability. In an aspect of FIG. 51b, the permeability is provided by an aperture 102 formed in the water retention layer 100B at its portion disposed above the active layer 12. In an aspect of FIG. 51c, the permeability is attained by rendering the water retention layer 100C thin to be, for example, about 2 nm.

Figure 52A:
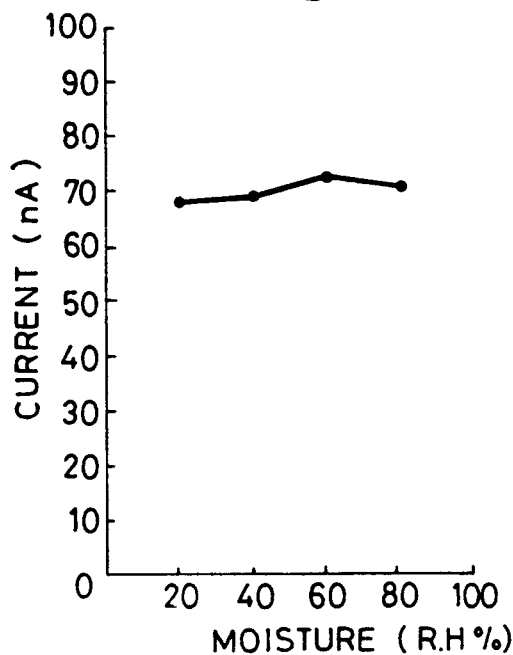
FIGS. 52a and 52b are graphs showing the relationship between the moisture and output current in the sensor of FIG. 50.
Figure 52B:
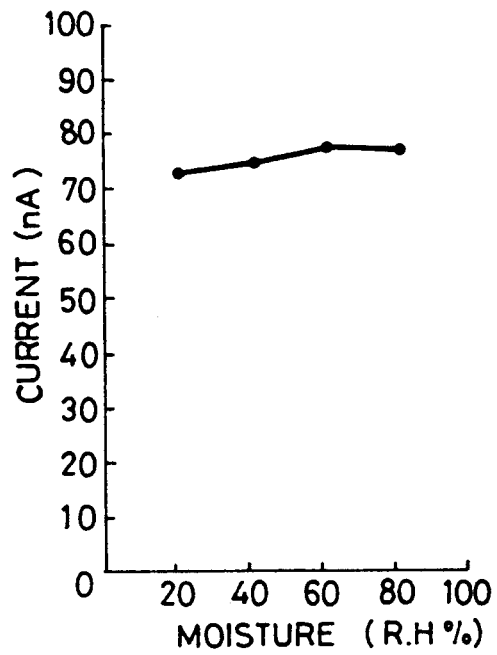
Figure 53:
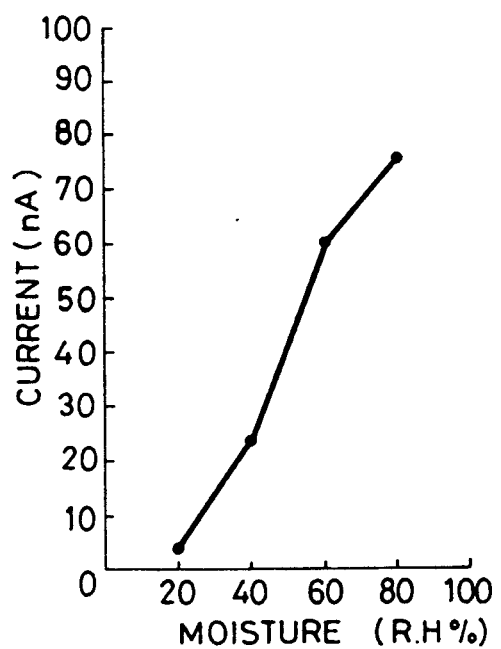
FIG. 53 is a graph showing the relationship between the moisture and output current in the sensor of FIG. 50 but the absence of a water retaining layer.

Characteristics of the gas sensor provided with the water retention layer 100 with respect to the humidity have been measured. A general use potentiostat was connected for a voltage application across the active electrode 12 and the reference electrode 14, CO gas was supplied at 1000 ppm while properly varying atmospheric temperature, and variation in the output current across the active and counter electrodes 12 and 13 was observed. In this case, with the gas sensor the water retention layer of which is formed by the NAFION/$H_2SO_4$ gelatinous substance, such results as shown in FIG. 52a could be obtained, while with the gas sensor of the water retention layer formed by the strach/acrylic acid gelationous substance such results as shown in FIG. 52b could be obtained. Similar measurement has been carried out with respect to a gas sensor having no water retention layer under the same conditions. As will be clear from a comparison of FIGS. 52a and 52b with FIG. 53 for the one having no water retention layer, it has been found that a stable detection output can be obtained according to the present invention.

According to a further feature of the present invention, there can be provided an arrangement which can realize a super minimization of the gas sensor. Referring to FIG. 54, in the present instance, the insulating substrate 11 and frame 15 in the foregoing embodiments are formed integral, and reactive portions 12a, 13a and 14a of the active, counter and reference electrodes 12, 13 and 14 are mounted inside a frame part 15A. Further, terminal portions 12b, 13b and 14b of the respective electrodes 12-14 are extended to the exterior from the frame part 15A, and the solid electrolyte layer 16 is provided over the reactive portions 12a, 13a and 14a inside the frame part 15A.

To be concrete, the gas sensor of the present embodiment may be prepared as in the followings. That is, as shown in FIG. 55a, first, a silicon dioxide film 112 for an etching is built up on top surface of a silicone substrate 111 through thermal oxidation to have a film thickness of 1 μm. A resist 113 is applied onto the etching-use silicon dioxide film 112 (see FIG. 55b) and is subjected to an exposure and development with a pattern corresponding to the shape of the frame part 15A (see FIG. 55c). Next, with the pattern of the resist 113 used as a mask, the silicon dioxide film 112 is subjected to a patterning and the silicon dioxide film 112 at other parts than the portion where the frame part 15A is to be formed is removed (see FIG. 55d). After removing the resist 113 (see FIG. 55e), the silicone substrate 111 is recessed with an etching liquid of KOH 45 wt. %, $H_2O$ 55 wt. % and a liquid temperature of 85° C., and the frame part 15A is formed (see FIG. 55f). So long as the formation is made in the pattern disposition of the silicon dioxide film 112, the recess can be made vertically into the surface of the silicone substrate 111 by means of the anisotropy of etching grate due to planar orientation of the silicone substrate 111, and the shape of the frame part 15A can be accurately formed. With an etching time of 30 minutes, the recessing of the silicone substrate 111 can be completed. When the remaining silicon dioxide film 112 is removed (see FIG. 55g), an integral body of the silicone substrate 111 and frame part 15A is to be formed.

Further, an insulating substrate part 11A is formed by building up a silicon dioxide layer 114 to be made as the insulating substrate part 11A through the thermal oxidation on the entire surface of the silicon substrate 111 including the frame part 15A to be of a thickness, for example, of 2 μm (see FIG. 55h). Then, the respective electrodes 12-14 is formed by, for example, Pt film to be 1 μm thick, for example, the solid electrolyte layer 16 is provided to cover them, and a gas sensor can be thereby formed.

In FIG. 56, there is shown another embodiment, in which the active, counter and reference electrodes 12-14 are formed inside a frame part 15B made integral with an insulating substrate part 11B, and the solid electrolyte layer 16 is provided to cover them. This gas sensor can be prepared, for example, by building up a mask 121 of a high polymer mask material or the like on a surface of an insulating substrate part 11B (see FIG. 57a), forming this mask 121 into a predetermined mask pattern (see FIG. 57b), thereafter forming the frame part 15B with the insulating substrate part 11B recessed employing properly an etching measure or the like (see FIG. 57c), removing the remaining mask 121 (see FIG. 57d), providing the respective electrodes, and covering them with the solid electrolyte layer.

In FIG. 58, there is shown still another embodiment, in which a recess is formed in an insulating substrate, the active, counter and reference electrodes 12-14 are formed within the recess, and then the recess is filled with the solid electrolyte layer 16. For this gas sensor, for example, a surface treatment is carried out in such that such insulating substrate 11C as shown in FIG. 59a is washed, thereafter an anisotropic etching is carried out, and then a recess 130 is formed so that mutually opposing two wall surfaces will be a slope as shown in FIG. 59b. With such provision of the slopes, it is made easier to adhere the electrode material through the sputtering or the like process. Then the sputtering and etching are carried out with respect to this insulating substrate 11C, and the active, counter and reference electrodes are formed as shown in FIG. 59c (only the active electrode 12 is shown in the drawing). In forming these electrodes, it may be executed by means of a screen printing or the like, but it is desirable for the purpose of minimizing the size of the sensor to provide over the entire surface of the recess 130 of the insulating substrate 11C a metallic material for the electrodes by means of such PVD process or the like as the sputtering, vacuum deposition or the like process, and to form a predetermined pattern of the electrodes through a photolithography to be about several $\mu$m thick. After the formation of the electrodes, the recess 130 is filled with the solid electrolyte layer 16 as shown in FIG. 59d. On this occasion, it is desirable for forming the solid electrolyte layer 16 several $\mu$m thick to employ a process of pouring the solid electrolyte layer 16 in a state of being dissolved by alcohol into the recess 130 and thereafter causing it to be set with alcohol removed.

According to still another feature of the present invention, there can be provided an arrangement capable of preventing that, when the insulating substrate is provided at its surface with unevenness in order to render the electrode surface to be uneven as in the embodiment of FIG. 13, the projections are of a width in the order of $\mu$m particularly in an ultra small gas sensor and are brittle and weak. That is, as shown in FIG. 60, such preparing process as referred to in the followings may be effectively employed in order to form at least the active electrodes 12 and counter electrodes 13 to be of a continuous unevenness at an interval of $\mu$m. Initially, as shown in FIG. 61a, an etching-use silicon dioxide layer 141 is built up on a surface of the insulating substrate 11 through the thermal oxidation, a resist 142 is applied thereover (see FIG. 61b), and the resist 142 is formed into a predetermined pattern by means of an exposure and development with the predetermined pattern for providing the active and counter electrodes with the projections (see FIG. 61c). Then, the silicon dioxide film 141 is subjected to a patterning with the foregoing pattern of the resist 142 used as the mask to remove the silicon dioxide film 141 at other portions than those where the projections are to be formed (see FIG. 61d), the resist 142 is then removed (see FIG. 61e), and the insulating substrate is recessed employing an etching liquid of KOH 45 wt. %, H$_2$O 55 wt. % and liquid temperature of 80° C. (see FIG. 61f). In this case, the patterned disposition of the silicon dioxide film 141 as in the above allows the recessing realized accurately vertically by means of the anisotropy of the etching due to the planar orientation of the insulating substrate 11, with an etching time of about 25 minutes. Then, the silicon dioxide layer 141 remaining is removed to form projections 143 (see FIG. 61g), a silicon dioxide film 144 is built up to be 1 $\mu$m through the same thermal oxidation as in the above over the entire surface of the insulating substrate 11 (see FIG. 61h), the uneven shape of the insulating substrate 11 is worked with the silicon dioxide film 144 removed by an etching with HF:H$_2$O=4:1 (see FIG. 61i), a silicon dioxide layer 145 to be made as an insulating layer is built up to be preferably 5000 Å thick over the entire surface of the insulating substrate 11 (see FIG. 61j), and the active, counter and reference electrodes consisting of Pt film or the like are formed (only the active electrode 12 is shown) through a mask sputtering process on top surface of the silicon dioxide layer 145 preferably to be 1 $\mu$m thick (see FIG. 61k).

In this case, as in FIG. 61g, the surface shape of the insulating substrate 11 is made vertical at rising portions of the projections from bottom face of recessed parts in the state where the silicon dioxide film 141 is removed as in FIG. 61g to have the projections 143 formed (see also FIG. 62a). Then, as the silicon dioxide film 144 is built up as in FIG. 61g, a stress is applied to the entire surface of the insulating substrate 11, and a distortion is yielded in the silicon dioxide film 144 at base portions of the projections 143, that is, at corners of the rising from the bottom face of recessed parts. However, the layer below this film 144 is formed as rounded as shown in FIG. 62b. Here, the silicon dioxide film 144 built up is removed, the projections 143 are made into a shape not easy to receive the stress, and thereafter the silicon dioxide layer 145 to be used as the insulating layer is built up, whereby it is made possible to prevent any such trouble as disconnection or the like from occurring in the electrodes formed on the insulating layer due to any damage in particular at the base portions of the projections 143, even when the recessed parts between the projections are made extremely small in the width upon minimization of the gas sensor (see also FIG. 62c).

According to still another embodiment of the present invention, further, there is provided an arrangement that allows the respective electrodes to be excellently formed with a photolithography employed for realizing an ultra minimization of the gas sensor. Referring first to FIG. 63, portions corresponding to the terminal parts 12b-14b (only the terminal part 12b of the active electrode is shown) for the respective electrodes 12-14 (only the active electrode 12 is shown) are formed in the form of projected bumps 150. In forming them, the bumps 150 of the insulating substrate 11D can be formed employing the process for forming the projections 30 or 143 on the top surface of the insulating substrate in the foregoing embodiment, the active, counter and reference electrodes 12-14 are formed on the entire surface of the insulating substrate 11D having the bumps 150, and a resist 151 is formed in a predetermined pattern thereon (see FIGS. 64a and 65a). This resist 151 covers the bumps 150 of the respective electrodes and is made to be of a pattern divided with the bottom parts interposed between the respective bumps 150. Here, a mask pattern 152 for causing the resist 151 to be exposed is formed in a shape covering over to outer side faces of the bumps 150, thereafter the electrode material is removed, and then the bumps 150 are entirely covered by the electrode material as shown in FIGS. 64b and 65b while the terminal parts 12b to 14b can be formed as mutually accurately divided, whereby the terminal parts 12b-14b can be formed as projected out of the electrolyte layer 16 when this layer 16 is provided, and the terminal parts 12b-14b can be prevented from coming into mutually contacting state through the layer 16 interposed. As the terminal parts 12b-14b are formed on the bumps 150 so as to be mutually reliably divided, it becomes unnecessary to provide the terminal parts 12b-14b to project out of the frame 15, respective parts of the electrodes can be formed inside the frame 15, and the gas sensor can be produced in a relatively simple manner, effectively utilizing the patterning technique by means of the photolithography process.

The terminal parts 12b-14b of the electrodes 12-14 can be prepared with a negative type resist. In this case, the mask pattern 152 is provided to cover the respective bumps 150 in the same manner as in such positive type as shown in FIGS. 64 and 65, and the resist 151 is provided while leaving the mask pattern 152 as shown in FIG. 66b. Thereafter, the electrode material is built up on the entire surface of the insulating substrate, the resist 151 is then removed, and the same electrodes 12-14 as in the foregoings are to be formed including the terminal parts 12b-14b provided on the bumps 150.

In the respective embodiments of FIG. 11 and following drawings, any arrangement and function references to which have been omitted are substantially the same as those of the respective materials, arrangements and functions of the respective parts in the sensor shown in FIG. 1, as would be readily appreciated. Further, any arrangement relating to a certain embodiment and shown only in any particular drawing may be applicable to any other embodiment as occasion demands. For example, the intermediate bonding layer 21 shown in FIG. 11 or the impermeable layer 80B shown in FIGS. 34 and 35 may be effectively employable in any other embodiment.

Upon using the electrochemical gas sensor according to the present invention, on the other hand, it has been found to be effective that, when the potential level from the potentiostat provided to the active electrode, for example, is made to be temporarily varied continuously for 10 to 20 times in a triangular wave form preferably in a range of $-0.5$ to $+1.0$ V, the substance produced upon the electrochemical reaction can be prevented from being build up in particular on the active electrode.

We claim:

1. An electrochemical gas sensor comprising an insulating substrate an active and counter electrodes mutually spaced and disposed on the same surface of said insulating substrate, said active and counter electrodes having respectively reactive portions, at least said reactive portion of said active electrode having on its surface a plurality of projections, a reference electrode made of gold spaced from said active and counter electrodes and having a reactive portion, a solid electrolyte layer formed to cover at least said reactive portions of said active, counter and reference electrodes including said projections of the active electrode, a gas barrier overlayer provided above said solid electrolyte layer, said overlayer having one small ventilating hole for providing gas permeability and for reducing ventilation to the electrodes to stabilize their sensibility to gases and an alumina filter layer disposed between the gas barrier overlayer and said solid electrolyte layer.

2. A sensor according to claim 1, wherein an intermediate bonding layer of a polycrystalline silicon is disposed between said insulating substrate and said electrodes.

3. A sensor according to claim 1, wherein said solid electrolyte layer consists of one selected from a group consisting of perfluorosulfonate polymer, polystyrene sulfonate, polyethylene sulfonate and polyvinyl sulfonate.

4. A sensor according to claim 1, wherein an intermediate bonding layer is disposed between said electrodes and said solid electrolyte layer.

5. A sensor according to claim 1 wherein said hole is located directly above said active electrode.

6. A sensor according to claim 1, wherein said solid electrolyte layer is provided with a moisture supply means for keeping the moisture content of the layer constant.

7. A sensor according to claim 6, wherein said moisture supply means comprises a storing chamber, and means for detecting the presence or absence of water is provided in said storing chamber.

8. A sensor according to claim 1, wherein a layer impermeable to moisture is disposed to cover said solid electrolyte layer for preventing moisture in the solid electrolyte layer from escaping to the exterior and limiting objective gas to be detected from diffusing into the solid electrolyte layer from the exterior.

9. A sensor according to claim 1, wherein an intermediate bonding layer of a polycrystalline silicon is disposed between said insulating substrate and said electrodes, and another intermediate bonding layer is disposed between said electrodes and said solid electrolyte layer.

10. A sensor according to claim 1, wherein an intermediate bonding layer is disposed between said electrodes and said solid electrolyte layer, an impermeable layer which prevents moisture in the solid electrolyte layer from escaping out to the exterior and limiting diffusion of objective gas to be detected into the solid electrolyte layer from the exterior, and said impermeable layer consists of one selected from a group consisting of fluoropolymer and hydrocarbon polymer.

11. A sensor according to claim 1, wherein an intermediate bonding layer of a polycrystalline silicon is disposed between said insulating substrate and said electrodes.

12. A sensor according to claim 1, wherein an intermediate bonding layer is disposed between said electrodes and said solid electrolyte layer, said intermediate bonding layer being of one selected from a group consisting of a silane coupling agent and a hydrophobic material.

13. A sensor according to claim 1, wherein an impermeable layer is provided to cover said solid electrolyte layer for preventing moisture in the solid electrolyte layer from escaping to the exterior and limiting diffusion of objective gas to be detected into the solid electrolyte layer from the exterior, said impermeable layer consisting of one selected from a group consisting of fluoropolymer and hydrocarbon polymer.

14. A sensor according to claim 1, wherein said reactive portion of said counter electrode is also provided on its surface with said projections covered by said electrolyte layer.

15. A sensor according to claim 14, wherein said projections have side faces and a top face and said solid electrolyte layer is thinner at portions from side faces to top face of the respective projections than that provided between the respective projections.

16. A sensor according to claim 1, wherein said projections have side faces and a top face and said solid electrolyte layer is thinner at portions from side faces to top face of the respective projections than that provided between the respective projections.

* * * * *

UNITED STATES PATENT AND TRADEMARK OFFICE
CERTIFICATE OF CORRECTION

PATENT NO. : 5,215,643

DATED : June 1, 1993

INVENTOR(S) : Kusanagi et al.

It is certified that error appears in the above-indentified patent and that said Letters Patent is hereby corrected as shown below:

Claim 1, column 25, line 32, change "an" to --and--.

Signed and Sealed this

Third Day of May, 1994

Attest:

BRUCE LEHMAN

Attesting Officer  Commissioner of Patents and Trademarks